(12) United States Patent
Kimball et al.

(10) Patent No.: US 12,344,626 B2
(45) Date of Patent: Jul. 1, 2025

(54) PHARMACEUTICAL COMPOUNDS AND THERAPEUTIC METHODS

(71) Applicant: RUTGERS, THE STATE UNIVERSITY OF NEW JERSEY, New Brunswick, NJ (US)

(72) Inventors: Spencer David Kimball, New Brunswick, NJ (US); Darren R. Carpizo, New Brunswick, NJ (US); John A. Gilleran, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 742 days.

(21) Appl. No.: 17/605,795

(22) PCT Filed: Apr. 22, 2020

(86) PCT No.: PCT/US2020/029379
§ 371 (c)(1),
(2) Date: Oct. 22, 2021

(87) PCT Pub. No.: WO2020/219587
PCT Pub. Date: Oct. 29, 2020

(65) Prior Publication Data
US 2022/0185827 A1 Jun. 16, 2022

Related U.S. Application Data

(60) Provisional application No. 62/837,707, filed on Apr. 23, 2019.

(51) Int. Cl.
| | | |
|---|---|---|
| C07F 3/00 | (2006.01) | |
| A61K 45/06 | (2006.01) | |
| C07D 213/68 | (2006.01) | |
| C07D 401/12 | (2006.01) | |
| C07D 405/12 | (2006.01) | |

(52) U.S. Cl.
CPC .............. C07F 3/003 (2013.01); A61K 45/06 (2013.01); C07D 213/68 (2013.01); C07D 401/12 (2013.01); C07D 405/12 (2013.01)

(58) Field of Classification Search
CPC ....... C07F 3/003; A61K 45/06; C07D 213/68; C07D 403/12; C07D 405/12
See application file for complete search history.

(56) References Cited

U.S. PATENT DOCUMENTS

| | | | |
|---|---|---|---|
| 4,657,903 | A | 4/1987 | Scovill et al. |
| 4,665,173 | A | 5/1987 | Klayman et al. |
| 4,777,166 | A | 10/1988 | Smith et al. |
| 7,112,680 | B2 | 9/2006 | Hofmann et al. |
| 10,221,133 | B2 | 3/2019 | Augeri et al. |
| 10,604,480 | B2 | 3/2020 | Augeri et al. |
| 10,604,481 | B2 | 3/2020 | Augeri et al. |
| 10,729,671 | B2 | 8/2020 | Augeri et al. |
| 10,828,288 | B2 | 11/2020 | Augeri et al. |
| 2008/0118576 | A1 | 5/2008 | Theodorescu et al. |
| 2013/0345164 | A1 | 12/2013 | Vazquez et al. |
| 2014/0142266 | A1 | 5/2014 | Sakamoto et al. |
| 2018/0000772 | A1 | 1/2018 | Augeri et al. |
| 2018/0000806 | A1 | 1/2018 | Augeri et al. |
| 2018/0002279 | A1 | 1/2018 | Augeri et al. |
| 2018/0002280 | A1 | 1/2018 | Augeri et al. |
| 2020/0096492 | A1 | 3/2020 | Loriau et al. |

FOREIGN PATENT DOCUMENTS

| | | |
|---|---|---|
| WO | 2001094340 A1 | 12/2001 |
| WO | 2006019955 A2 | 2/2006 |
| WO | 2006101740 A2 | 9/2006 |
| WO | 2007035489 A2 | 3/2007 |
| WO | 2009039553 A1 | 4/2009 |
| WO | 2012175962 A1 | 12/2012 |
| WO | 2015021456 A1 | 2/2015 |
| WO | 2016123242 A1 | 8/2016 |
| WO | 2016123246 A1 | 8/2016 |
| WO | 2016123250 A1 | 8/2016 |
| WO | 2016123253 A1 | 8/2016 |
| WO | 2020219589 A1 | 10/2020 |

OTHER PUBLICATIONS

Loh, S , "Follow the Mutations: Toward Class-Specific, Small-Molecule Reactivation of p53", Biomolecules 10, 303, 1-14 (2020).
Agrawal, K , et al., "Potential antitumor agents. 13. 4-Methyl-5-amino-1-formylisoquinoline thiosemicarbazone", Journal of Medicinal Chemistry 19(7), 970-972 (1976).
Antonini, I , et al., "Elucidation of the structure of the antineoplastic agents, 2-formylpyridine and 1-formylisoquinoline thiosemicarbazones", Journal of Medicinal Chemistry 20(3), 447-449 (1977).
Bellitto, C , et al., "Conformational Studies of Some Potentially Bidentate Thiosemicarba-zones and Related Complexes of Zinc(II)", J.C.S. Dalton 68570(21), 758-762 (1976).
Bermejo, E , et al., "Complexes of Grup 12 Metals with 2-Acetylpyridine 4N-Dimethyl-thiosemiearbazone and with 2-Acetyipyridine-N-oxide 4N-Dimethyl-thiosemiearbazone: Synthesis, Structure and Antifungal Activity", Zeitschrift fuer Naturforschung, B: Chemical Sciences 54(6), 777-787 (1999).

(Continued)

*Primary Examiner* — Shirley V Gembeh
(74) *Attorney, Agent, or Firm* — Viksnins Harris Padys Malen LLP

(57) ABSTRACT

The invention provides a complex comprising $Zn^{2+}$ and a compound of formula (I): or a deuterated analog thereof, or an ion or poly-ion thereof, or a salt thereof that is useful for treating cancer, as well as compositions and kits comprising such complexes.

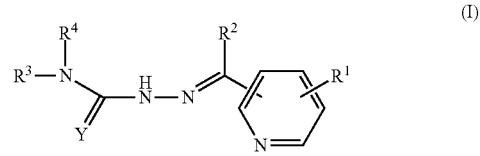

(I)

16 Claims, No Drawings

(56) References Cited

OTHER PUBLICATIONS

Bjelogrlic, S., et al., "Synthesis, structure and characterization of novel Cd(II) and Zn(II) complexes with the condensation product of 2-formylpyridine and selenosemicarbazide Antiproliferative activity of the synthesized complexes and related selenosemicarbazone complexes", Journal of Inorganic Biochemistry 104, 673-682 (2010).

Blanden, A., et al., "Synthetic Metallochaperone ZMC1 Rescues Mutant p53 Conformation by Transporting Zinc into Cells as an Ionophore", Mol Pharmacol 87, 825-831 (2015).

Chhabra, N., et al., "A review of drug isomerism and its significance", Int J Appl Basic Med Res 3(1), 16-18 (2013).

Chun-Ying, D., et al., "Synthesis, Crystal Structure and Nonlinear Optical Properties of Thiosemicarbazone Zinc Complex", J Coord Chem 47, 433-439 (1999).

Easmon, J., et al., "2-benzoxazolyl and 2-benzimidazolyl hydrazones derived from 2-acetylpyridine: a novel class of antitumor agents", Int J Cancer 94, 89-96 (2001).

Easmon, J., et al., "Synthesis, Structure—Activity Relationships, and Antitumor Studies of 2-Benzoxazolyl Hydrazones Derived from Alpha-(N)-acyl Heteroaromatics", J Med Chem 49, 6343-6350 (2006).

Easmon, J., et al., "Thiazolyl and benzothiazolyl hydrazones derived from α-(N)-acetylpyridines and diazines: synthesis, antiproliferative activity and CoMFA studies", Eur J Med Chem 32, 397-408 (1997).

File Caplus, "Preparation and characterization of vanillin thiosemicarbazone complexes with cobalt(II), nickel(II), copper(II), zinc(II), cadmium(II), and mercury(II)", STN CA Caesar Accession No. 1170, 2 pages (1984).

File Caplus, "Synthesis and crystal structure of zinc(II) complex [Zn(25-MBTSC)212]", STN CA Caesar Accession No. 1162, 1 page (2013).

File Caplus, "Synthesis and structure of 1.5Zn(phen)3.cntdot.L.cntdot..3N03 supramolecule (phen=o-phenanthroline, L=4-aminoacetophenone thiosemicarbazone", STN CA Caesar Accession No. 1176, 2 pages (2008).

Gudasi, K., et al., "Synthesis and spectral investigation of some transition metal complexes containing pentadentate macroacyclic NNNNN-donor Schiff base ligands", Transition Metal Chemistry 30, 726-732 (2005).

Hall, I, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).

Heit, et al., "Substituted Hydrazones as Tridentate Chelating Agents", Analytica Chimica Acta 32, 448-455 (1965).

Huang, H., et al., "A Series of α-Heterocyclic Carboxaldehyde Thiosemicarbazones Inhibit Topoisomerase IIα Catalytic Activity", Journal of Medicinal Chemistry 53, 3048-3064 (2010).

Huang, Y., et al., "Correlating gene expression with chemical scaffolds of cytotoxic agents: ellipticines as substrates and inhibitors of MDR1", Pharmacogenomics Journal 5, 112-125 (2005).

Ibrahim, A., et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).

Kalinowski, D., et al., "Design, Synthesis, and Characterization of Novel Iron Chelators: Structure—Activity Relationships of the 2-Benzoylpyridine Thiosemicarbazone Series and Their 3-Nitrobenzoyl Analogues as Potent Antitumor Agents", Journal of Medicinal Chemistry 50(15), 3716-3729 (2007).

Khalaji, A., et al., "Synthesis and Characterization of Zinc(II) Complexes with 3,4-Dimethoxybenzaldehyde Thiosemicarbazone: The Crystal Structure of [Zn(34-MBTSC) 2 Cl 2 ]", Phosphorus, Sulfur, and Silicon 188, 1119-1126 (2013).

Khaled, S., et al., "Synthesis and Spectroscopic Characterization of Some NOvel Polypyridine and Phenanthroline Complexes of Mn(II), Fe(II), Co(II) and Zn(II) Incorporating a Bidentate Benzothiazolyl Hydrazone Ligand", Chem Sci Trans 2(4), 1222-1231 (2013).

Kodela, R., et al., "Positional Isomers of Aspirin are Equally Potent in Inhibiting Colon Cancer Cell Growth: Differences in Mode of Cyclooxygenase Inhibition", J Pharmacol Exp Ther 346, 85-94 (2013).

Kovala-Demertzi, D., et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).

Mohan, M., et al., "Synthesis, Characterization, and Antitumor Properties of some Metal Complexes of 2,6-Diacetylpyridine Bis(N4-azacyclic Thiosemicarbazone)", Journal of Inorganic Biochemistry 34, 41-54 (1988).

Moorthy, N., et al., "QSAR analysis of 2-benzoxazolyl hydrazone derivatives for anticancer activity and its possible target prediction", Med Chem Res 21, 133-144 (2012).

Mrozek-Wilczkiewicz, A., et al., "Iron Chelators in Photodynamic Therapy Revisited: Synergistic Effect by Novel Highly Active Thiosemicarbazones", ACS Medicinal Chemistry Letters 5(4), 336-339 (2014).

Odashima, T., et al., "Determination of Microamounts of Iron by Extraction-Spectrophotometry with 2-Acetylpyridine-2-benzothiazolylhydrazone and Its Sensitization by Employing an Analog Derivative Technique", Microchemical Journal 33, 138-146 (1986).

Patani, George A., et al., "Bioisosterism: A Rational Approach in Drug Design", Chem Rev 96, 3147-3176 (1996).

Patent Cooperation Treaty, International Search Report and Written Opinion for PCT/US2000/029379, 10 pages, dated Sep. 9, 2020.

Priyadharsini, R., et al., "Docking, synthesis, characterization and evaluation of novel cdk2 inhibitors: benzothiazole derivatives", International Journal of Pharmacy and Pharmaceutical Sciences 4(3), 574-585 (2012).

Pubchem, "[(Z)-(5-Amino-4-morpholin-4-ylisoquinolin-1-yl)methylideneamino]thiourea", PubChem CID: 44355883, 8 pages, (Nov. 19, 2009).

Rao, P., et al., "Synthesis and Spectroscopic Studies on a Dibasic Pent Dentate Ligand", Inorganic Chemistry 1 (3), 47-52 (2006).

Ren, P., et al., "A new approach to suppress nonlinearity-transparency trade-off through coordination chemistry: syntheses and spectroscopic study on second-order nonlinear optical properties of a series of square-pyramidal zinc (II) complexes", Spectrochimica Acta Part A 59, 1095-1101 (2003).

Richardson, D., et al., "Dipyridyl Thiosemicarbazone Chelators with Potent and Selective Antitumor Activity Form Iron Complexes with Redox Activity", J Med Chem 49, 6510-6521 (2006).

Ruangpornvisuti, V., et al., "A DFT investigation of conformational geometries and interconversion equilibria of phenylthiosemicarbazone and its complexation with zinc", J Mol Model 10, 418-426 (2004).

Singh, K., et al., "Stereochemistry and Its Role in Drug Design", IJPSR 5(11), 4644-4659 (2014).

Sleebs, B., et al., "Discovery of Potent and Selective Benzothiazole Hydrazone Inhibitors of Bcl-XL", J Med Chem 56, 5514-5540 (2013).

STN Record, Accession No. 1975:461709, JP49126728, 1 page (1975).

Tian, Y., et al., "Structural characterization and second-order nonlinear optical properties of zinc halide thiosemicarbazone complexes", Polyhedron 21, 1217-1222 (2002).

Todorovic, T., et al., "Synthesis and characterization of Zn(II) and Cd(II) complexes with 2,6-diacetylpyridine-bis (selenosemicarbazone). Crystal structure of a Ni(II) complex with a modified 2,6-diacetylpyridine-bis (selenosemicarbazone)", Inorganic Chemistry Communications 9, 862-865 (2006).

Vartale, S., et al., "Synthesis and Antimicrobial Activity of 6/7/8-Substituted-1-[ARYL/6' Substituted-2'-Benzothiazolyl]-Pyrazolo [4,5-b] Quinolines", Indian Journal of Heterocyclic Chemistry 16, 163-166 (2006).

(56) References Cited

OTHER PUBLICATIONS

Webster, D , et al., "Synthesis and characterization of novel pentagonal bipyramidal compleses of iron(II), cobalt(II), and zinc(II)", Journal of American Chemical Society 95(19), 6505-6506 (1973).
Yu, X , et al., "Allele-Specific p53 Mutant Reactivation", Cancer Cell 21, 614-625 (2012).
Yu, X , et al., "Small molecule restoration of wildtype structure and function of mutant p53 using a novel zinc-metallochaperone based mechanism", Oncotarget 5(19), 8879-8892 (2014).
U.S. Appl. No. 15/545,966, U.S. Pat. No. 10,221,133.
U.S. Appl. No. 16/253,126, U.S. Pat. No. 10,604,481.
U.S. Appl. No. 15/545,968, U.S. Pat. No. 10,604,480.
U.S. Appl. No. 15/545,971, U.S. Pat. No. 10,828,288.
U.S. Appl. No. 15/545,975, U.S. Pat. No. 10,729,671.
U.S. Appl. No. 17/605,750, 2022-0096492.

PHARMACEUTICAL COMPOUNDS AND THERAPEUTIC METHODS

PRIORITY OF INVENTION

This application claims priority to U.S. Provisional Application No. 62/837,707, filed 23 Apr. 2019. The entire content of this application is incorporated herein by reference.

STATEMENT REGARDING FEDERALLY SPONSORED RESEARCH

This invention was made with government support wider CA200800 awarded by the National Institutes of Health. The Government has certain rights in this invention.

BACKGROUND OF THE INVENTION

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics. Currently there is a need for additional cancer therapeutics. In particular, there is a need for cancer therapeutics with acceptable solubility that can reactivate mutant p53.

SUMMARY OF THE INVENTION

This invention provides novel complexes, kits, and methods directed toward refolding TP53 mutant proteins into their wild-type conformations by treatment with zinc(II) metallo-chaperone complexes.

More specifically, one aspect of the present invention provides a complex of the invention, which is a complex comprising $Zn^{2+}$ and a compound of formula (I):

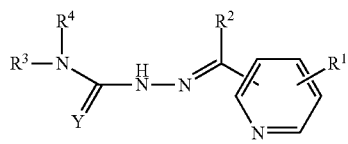

(I)

or a deuterated analog thereof, or an ion or poly-ion thereof, or a salt of said complex, wherein:
  $R^1$ is $(C_1-C_6)$alkoxy, $(C_3-C_6)$cycloalkyoxy, or $-OR^5$ wherein any $(C_1-C_6)$alkoxy or $(C_3-C_6)$cycloalkyoxy is substituted with one or more groups independently selected $-N(R^a)_2$ and $(C_1-C_6)$alkoxy;
  $R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, $(C_3-C_6)$cycloalkyl and $C_4-C_6$ heterocycloalkyl, is optionally substituted with one or more groups independently selected from halo, $-N(R^b)_2$, $(C_3-C_6)$cycloalkyl, $(C_1-C_6)$alkoxy, $(C_2-C_6)$alkanoyloxy, $(C_2-C_6)$ alkoxycarbonyl, $(C_2-C_6)$ alkylaminocarbonyl, and $(C_2-C_6)$ alkanoylamino;
  $R^3$ and $R^4$ are each independently selected from H, $(C_1-C_6)$alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;
  $R^5$ is a 4-7 membered heterocyclyl;
  Y is S, O, or Se;
  each $R^a$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, $(C_2-C_6)$ alkoxycarbonyl, $(C_2-C_6)$ alkylaminocarbonyl, and $(C_2-C_6)$ alkanoylamino is optionally substituted with one or more groups independently selected from halo, $(C_3-C_6)$cycloalkyl, and $(C_1-C_6)$alkoxy; or two $R^a$ taken together with the nitrogen to which they are attached form a azetidino, pyrrolidino, piperidine, or morpholino ring; and
  each $R^b$ is independently selected from the group consisting of H, $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkylaminocarbonyl and $(C_1-C_6)$alkoxycarbonyl, wherein any $(C_1-C_6)$alkyl, $(C_3-C_6)$alkenyl, $(C_3-C_6)$alkynyl, $(C_3-C_6)$cycloalkyl, $(C_1-C_6)$alkanoyl, and $(C_1-C_6)$alkoxycarbonyl, $(C_1-C_6)$ alkylaminocarbonyl, and $(C_2-C_6)$ alkanoylamino is optionally substituted with one or more groups independently selected from halo, $(C_3-C_6)$cycloalkyl, and $(C_1-C_6)$alkoxy; or two $R^a$ taken together with the nitrogen to which they are attached form a ring, e.g., azetidino, pyrrolidino, piperidine, or morpholino;
provided the compound of formula (I) is not:

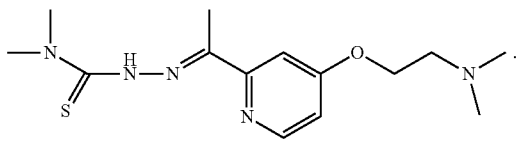

Another aspect of the present invention provides a complex, which is a complex comprising $Zn^{2+}$ and a compound of formula (I):

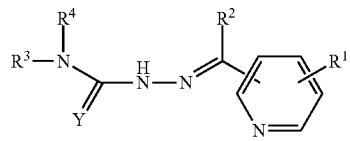

or a deuterated analog thereof, or an ion or poly-ion thereof, or a salt of said complex, wherein:
  $R^1$ is $(C_1-C_6)$alkoxy or $(C_3-C_6)$cycloalkyoxy, wherein any $(C_1-C_6)$alkoxy or $(C_3-C_6)$cycloalkyoxy is substituted with one or more groups independently selected $-N(R^a)_2$ and $(C_1-C_6)$alkoxy;
  $R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, ($C_3$-$C_6$)cycloalkyl and $C_4$-$C_6$ heterocycloalkyl, is optionally substituted with one or more groups independently selected from halo, —N($R^b$)$_2$, ($C_3$-$C_6$)cycloalkyl, ($C_1$-$C_6$)alkoxy, ($C_2$-$C_6$)alkanoyloxy, ($C_2$-$C_6$) alkoxycarbonyl, ($C_2$-$C_6$) alkylaminocarbonyl, and ($C_2$-$C_6$) alkanoylamino;

$R^3$ and $R^4$ are each independently selected from H, ($C_1$-$C_6$)alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;

Y is S, O, or Se;

each $R^a$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$) alkoxycarbonyl, wherein any ($C_1$-$C_6$)alkyl, ($C_2$-$C_6$) alkenyl, ($C_2$-$C_6$)alkynyl, ($C_3$-$C_6$)cycloalkyl, ($C_1$-$C_6$) alkanoyl, and ($C_1$-$C_6$)alkoxycarbonyl, ($C_2$-$C_6$) alkoxycarbonyl, ($C_2$-$C_6$) alkylaminocarbonyl, and ($C_2$-$C_6$) alkanoylamino is optionally substituted with one or more groups independently selected from halo, ($C_3$-$C_6$) cycloalkyl, and ($C_1$-$C_6$)alkoxy; or two $R^a$ taken together with the nitrogen to which they are attached form a azetidino, pyrrolidino, piperidino, or morpholino ring; and each $R^b$ is independently selected from the group consisting of H, ($C_1$-$C_6$)alkyl, ($C_3$-$C_6$)alkenyl, ($C_3$-$C_6$)alkynyl, ($C_3$-$C_6$)cycloalkyl, ($C_1$-$C_6$)alkanoyl, ($C_1$-$C_6$)alkylaminocarbonyl and ($C_1$-$C_6$)alkoxycarbonyl, wherein any ($C_1$-$C_6$)alkyl, ($C_3$-$C_6$)alkenyl, ($C_3$-$C_6$)alkynyl, ($C_3$-$C_6$)cycloalkyl, ($C_1$-$C_6$)alkanoyl, and ($C_1$-$C_6$)alkoxycarbonyl, ($C_1$-$C_6$) alkylaminocarbonyl, and ($C_2$-$C_6$) alkanoylamino is optionally substituted with one or more groups independently selected from halo, ($C_3$-$C_6$) cycloalkyl, and ($C_1$-$C_6$)alkoxy; or two $R^a$ taken together with the nitrogen to which they are attached form a ring, e.g., azetidino, pyrrolidino, piperidino, or morpholine;

provided the compound of formula (I) is not:

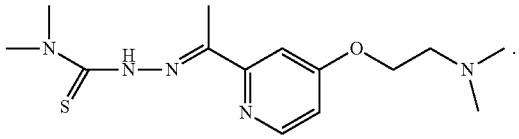

Another aspect of the present invention provides a salt (e.g. a pharmaceutically acceptable salt) of a complex comprising and a compound of formula (I) or an ion or poly-ion thereof.

Another aspect of the present invention provides a method of inhibiting cancer cell growth comprising administering to a human afflicted with cancer, an amount of a complex of the invention having a $Zn^{2+}$ ion.

Another aspect of the present invention provides a method comprising:

combining $Zn^{2+}$ ions and a monomer of formula (I) in a ratio of 2:1 (monomer:zinc) to form a neutral complex, or forming a pharmaceutically acceptable salt of such neutral complex; and diffusing the complex or the salt across a plasma membrane of a cell under conditions where the $Zn^{2+}$ ion will bind to a native ligation site of a mutant p53 inside the cell.

Another aspect of the present invention provides a pharmaceutical composition comprising, in a pharmaceutically acceptable carrier, a compound or complex to release zinc to p53.

Another aspect of the present invention provides a method of inhibiting cancer cell growth, comprising administering to an animal (e.g. a human), an effective amount of a compound or complex as described herein.

Another aspect of the present invention provides a method of inhibiting cancer cell growth, comprising administering to a human in need thereof, an effective amount of a complex as described herein and further comprising administering to the human a zinc supplement.

Another aspect of the present invention provides a method of inhibiting cancer cell growth comprising administering to a human afflicted with cancer, an amount of a neutral complex of the invention having a $Zn^{2+}$ ion or a pharmaceutically acceptable salt of such a neutral complex, effective to inhibit growth of cancer cells in the human.

Another aspect of the present invention provides a method comprising: binding a $Zn^{2+}$ ion to a monomer of formula (I) in a ratio of 2:1 (monomer:zinc) to form a complex outside a cell; diffusing the complex or a pharmaceutically acceptable salt thereof, including the $Zn^{2+}$ ion across a plasma membrane of the cell; and binding the $Zn^{2+}$ ion to a native ligation site of a mutant p53 inside the cell.

The invention further includes methods of preparing, methods of separating, and methods of purifying of the complexes described herein.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —C₆H₅.

The term "heterocyclyl" or "heterocycle" as used herein refers to a single saturated or partially unsaturated ring. The term includes single saturated or partially unsaturated rings (e.g., 4, 5, 6 or 7-membered rings) from about 2 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl. In one embodiment heterocyclyl is a 5-membered heterocyclyl or 6-membered heterocyclyl. In one embodiment heterocyclyl is a 5-membered heterocyclyl.

Deuterated

The term "deuterated" means enriched in deuterium above its natural abundance at one or more positions of a compound. When a particular position, for example, a carbon atom, is deuterated, it is understood that the abundance of deuterium at that position is substantially greater than the natural abundance of deuterium, which is 0.015%. A deuterated position typically has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a compound has an isotopic enrichment factor of at least 3500 (52.5% deuterium incorporation) at a given deuterated atom, at least 4000 (60% deuterium incorporation), at least 4500 (67,5% deuterium incorporation), at least 5000 (75% deuterium incorporation), at least 5500 (82.5% deuterium incorporation), at least 6000 (90% deuterium incorporation), at least 6333.3 (9.5% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

It is to be understood that a deuterated compound contains one or more deuterium atoms. For example, a deuterated compound may contain just one deuterium. In some embodiments, a deuterated compound contains just two deuteriums. In some embodiments, a deuterated compound contains only three deuteriums. In some embodiments, a deuterated compound contains four deuteriums. In some embodiments, a deuterated compound contains 1, 2, 3, or 4 deuteriums, or any range derivable therein.

Deuterium can be incorporated into a compound of formula (I) using a variety of known reagents and synthetic techniques. For example, deuterium can be incorporated into a compound of formula (I) using LiAlD₄. It can also be incorporated into a compound of formula (I) such as through reduction, catalytic hydrogenation or isotopic exchange using appropriate deuterated reagents such as deuterides, D₂ and D₂O.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

It will further be appreciated by those skilled in the art that compounds of formula (I) can exist in a cis-conformation (Formula (Iy)) and in a trans-conformation (formula (Ix),

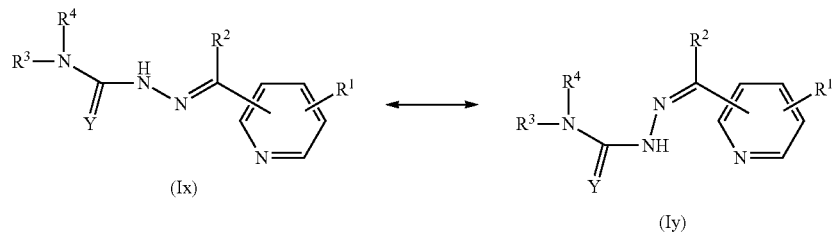

(Ix) (Iy)

which may interconvert and which may be in equilibrium in solution. It is understood that the compounds of formula (I) and formulae (Ia-Ig) include both conformations, with a specific conformation being identified as either formula (Ix) or formula (Iy).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; and $(C_3-C_6)$cycloalkoxy can be cyclopropyloxy, cyclobutyloxy, cyclopentyloxy, or cyclohexyloxy.

In one specific embodiment, the compound of formula (I) is a compound of formula (Ia):

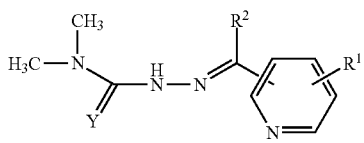

or an ion or poly-ion thereof.

In one specific embodiment, the compound of formula (I) is a compound of formula (Ib):

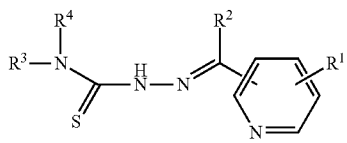

or an ion or poly-ion thereof.

In one specific embodiment, the compound of formula (I) is a compound of formula

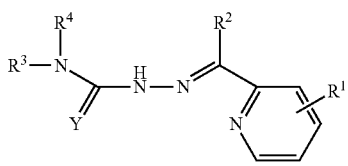

or an ion or poly-ion thereof.

In one specific embodiment, the compound of formula (I) is a compound of formula (Id):

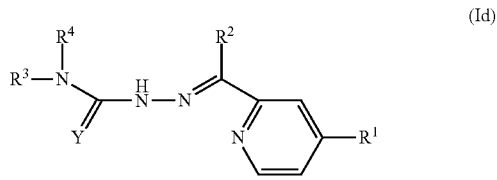

or an ion or poly-ion thereof.

In one specific embodiment, the compound of formula (I) is a compound of formula (Ie):

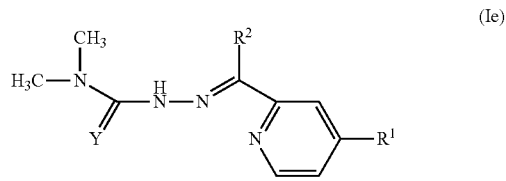

or an ion or poly-ion thereof.

In one specific embodiment, the compound of formula (I) is a compound of formula

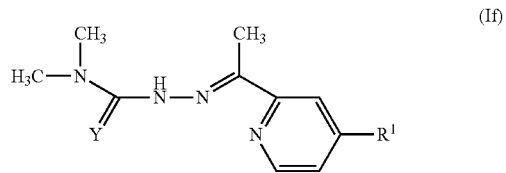

or an ion or poly-ion thereof.

In one specific embodiment, the compound of formula (I) is a compound of formula (Ig):

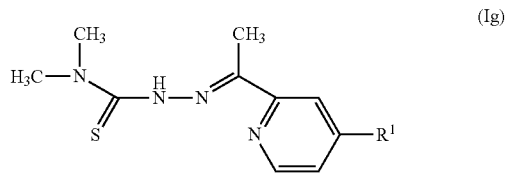

or an ion or poly-ion thereof.

In general, a zinc complex of the invention can be prepared as illustrated in the following scheme.

General Synthesis of 2:1 Zinc Complexes

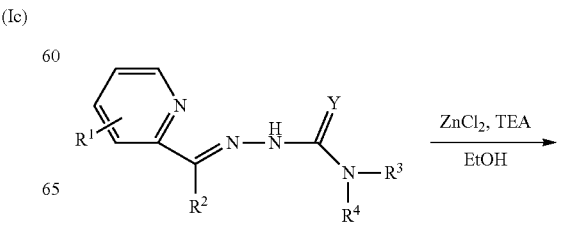

-continued

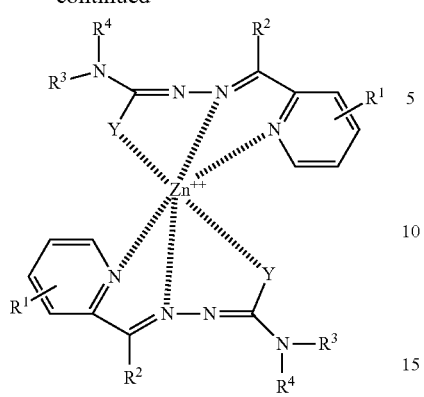

The invention will now be illustrated by the following non-limiting Examples.

EXAMPLES

Example 1

Synthesis of Complex (ZN-8)

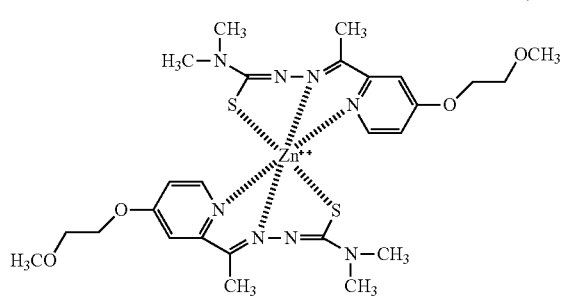

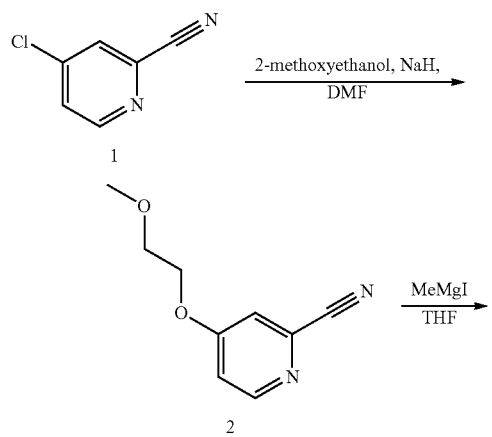

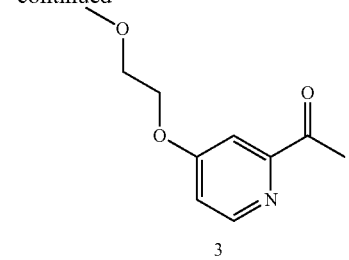

a. Preparation of 4-(2-methoxyethoxy)picolinonitrile (2)

To a solution of 2-methoxyethanol (1.14 ml, 14.4 mmol, 1 eq) in 50 ml DMF at 0° C. was added sodium hydride (60% suspension, 692 mg, 17.73 mmol, 1.2 eq). After stirring for 5 min at 0° C. a solution of 4-chloropicolinonitrile (1) (2.0 g. 14.4 mmol, 1 eq) in 5 ml DMF was added. The reaction was allowed to slowly warm to room temperature and stirred overnight. Upon determining that the reaction was ~75% complete by LC/MS, additional sodium hydride (60%, 200 mg, 5 mmol) and 2-methoxyethanol (350 ul, 4.4 mmol) were added. After stirring for 1 hour at room temperature, the reaction was determined complete by LC/MS and quenched with water. The reaction was concentrated under reduced pressure to remove the majority of the DMF present. The concentrate was partitioned in EtOAc/water. The organic was washed 2× water, 1× brine. The aqueous layers were re-extracted with EtOAc to isolate any product remaining in aqueous. The organic extracts were combined, dried over sodium sulfate, filtered and concentrated. The residue was purified by silica gel chromatography (25%→50% EtOAc/Hex) to give 4-(2-methoxyethoxy)picolinonitrile (2) (2.15 g, 86% purity by LC/MS) as a yellow oil. MS: 201.35 [M+Na]$^+$.

b. Preparation of 1-(4-(2-methoxyethoxy)pyridin-2-yl)ethan-1-one (3)

To a solution of 4-(2-methoxyethoxy)picolinonitrile (2) (2.15 g, 12.1 mmol, 1 eq) in 45 ml THF at 0° C. was added MeMgI (3M in Et$_2$O, 6.1 ml, 18.2 mmol, 1.5 eq). After warming and stirring for 1 hour at room temperature, the reaction was determined complete by LC/MS and quenched with water. The reaction was adjusted to pH=2 with 1M HCl and stirred overnight. The reaction was partitioned in EtOAc/water and the aqueous was extracted 2× EtOAc. The combined organics were dried over sodium sulfate, concentrated under reduced pressure and purified by silica gel chromatography (25%→50% EtOAc/Hex). Product fractions were combined and concentrated to give 1-(4-(2-methoxyethoxy)pyridin-2-yl)ethan-1-one (3) (1.41 g, 99% purity by LC/MS) as a clear oil. MS: 217.00 [M+Na]$^+$.

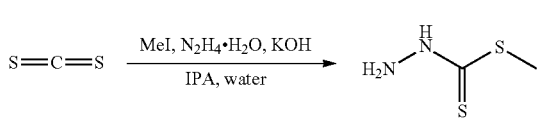

c. Preparation of methyl hydrazinecarbodithioate (6)

To a solution of KOH (5.6 g, 100 mmol, 1 eq) in 10 ml water was added 10 ml isopropanol. The reaction was cooled to 0° C. and all subsequent additions were performed at this temperature. Hydrazine hydrate (6.15 ml, 100 mmol, 1 eq) was added and the solution was stirred for 30 min. After dropwise addition of carbon disulfide (6.04 ml, 100 mmol, 1 eq) over 30 min, the reaction was stirred for 1 hour. Methyl iodide was added dropwise over 30 min and the reaction was allowed to stir for 1 hour. The white solid formed in the reaction was filtered and washed with ice water. The solid was dried under vacuum, dissolved in dichloromethane, dried over sodium sulfate, filtered and concentrated. The concentrate was recrystallized from dichloromethane and filtered to give methyl hydrazinecarbodithioate (6) (5.25 g, 43% yield) as a white crystalline solid.

d. Preparation of methyl (E)-2-(1-(4-(2-methoxyethoxy)pyridin-2-yl)ethylidene)hydrazine-1-carbodithioate (7)

A solution of 1-(4-(2-methoxyethoxy)pyridin-2-yl)ethan-1-one (3) (1.41 g, 7.22 mmol, 1 eq) and methyl hydrazinecarbodithioate (6) (970 mg, 7.94 mmol, 1.1 eq) in 15 ml isopropanol was heated overnight at 60° C. The reaction was determined complete by LC/MS and cooled to room temperature. The precipitated solid was filtered, washed with isopropanol and dried under vacuum to give methyl (E)-2-(1-(4-(2-methoxyethoxy)pyridin-2-yl)ethylidene)hydrazine-1-carbodithioate (7) (2.2 g, quantitative yield, 99% purity by LC/MS) as a light yellow solid. MS: 299.41 [M+H]$^+$, MS: 321.85 [M+Na]$^+$.

e. Preparation of (E)-2-(1-(4-(2-methoxyethoxy)pyridin-2-yl)ethylidene)-N,N-dimethylhydrazine-1-carbothioamide (8)

Methyl (E)-2-(1-(4-(2-methoxyethoxy)pyridin-2-yl)ethylidene)hydrazine-1-carbodithioate (7) (2.16 g, 7.22 mmol) was dissolved in 10 ml EtOH, 5 ml dimethylamine (40% in water) and heated overnight at 60° C. in a sealed reaction vessel. The reaction was determined complete by LC/MS and cooled to room temperature. The crude reaction was concentrated and purified by silica gel chromatography (2%→5%→10% MeOH/DCM). Product containing fractions were concentrated and recrystallized from EtOH to afford (E)-2-(1-(4-(2-methoxyethoxy)pyridin-2-yl)ethylidene)-N,N-dimethylhydrazine-1-carbothioamide (8) (1.08 g, 99% purity by LC/MS) as a light yellow solid. $^1$H NMR (400 MHz, DMSO-d6) δ 9.59 (s, 1H), 8.60-8.39 (m, 1H), 7.55-7.25 (m, 1H), 7.19-7.00 (m, 1H), 4.34-4.28 (m, 1H), 4.24-4.18 (m, 1H), 3.69 (tt, J=6.7, 2.4 Hz, 2H), 3.34-3.30 (m, 9H), 2.62 (d, J=1.0 Hz, 1H), 2.36 (d, J=6.8 Hz, 2H). Note: Peaks have complex splitting from multiple conformational isomers. MS: 296.85 [M+H]$^+$, MS: 318.70 [M+Na]$^+$.

f. Preparation of Zn[(E)-2-(1-(4-(2-methoxyethoxy)pyridin-2-yl)ethylidene)-N,N-dimethylhydrazine-1-carbothioamide]$_2$ (ZN-8)

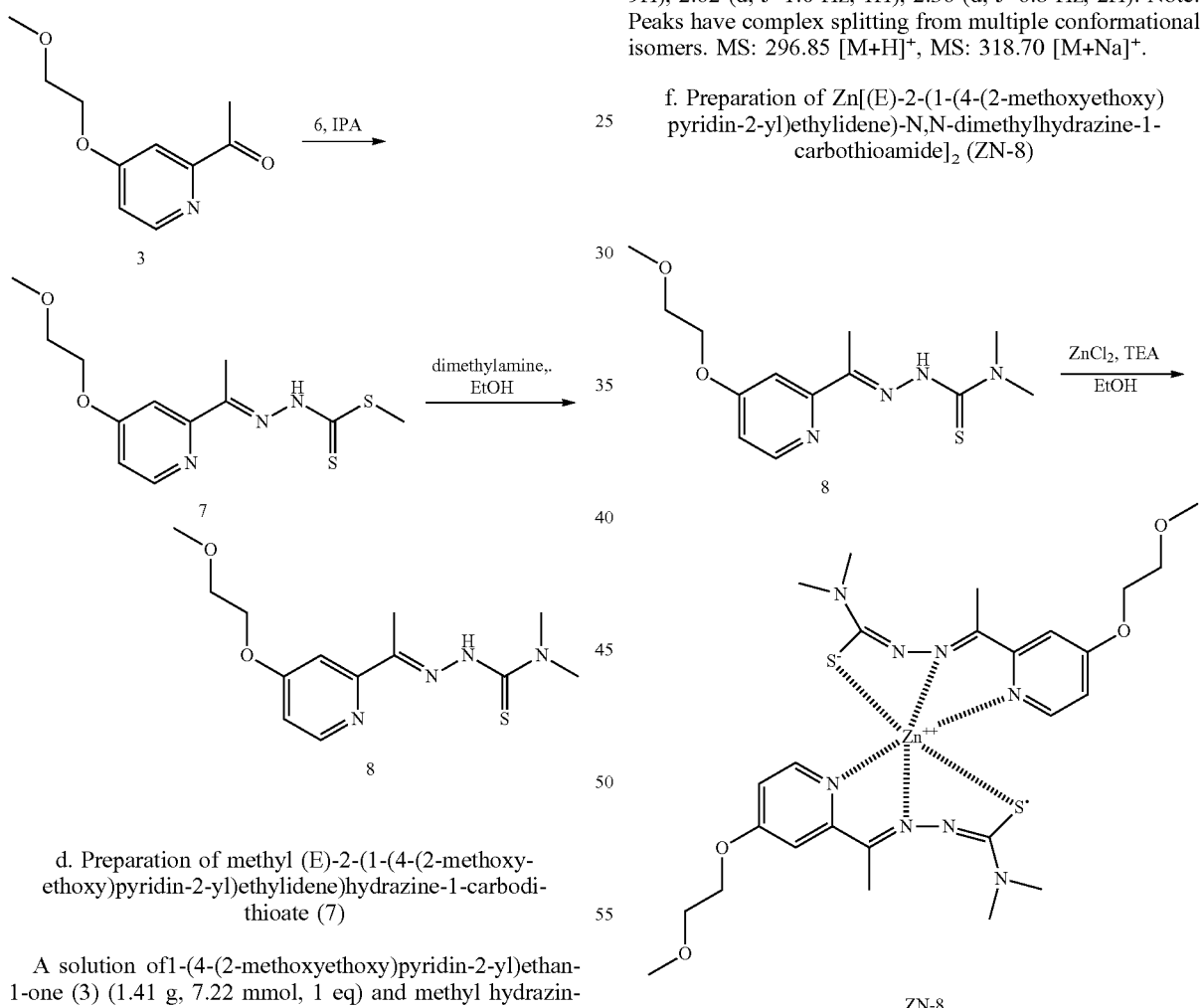

To a suspension of (E)-2-(1-(4-(2-methoxyethoxy)pyridin-2-yl)ethylidene)-N,N-dimethylhydrazine-1-carbothioamide (8) (1.08 g, 3.64 mmol, 1 eq) and zinc chloride (248 mg, 1.82 mmol, 0.5 eq) in 30 ml EtOH was added 2 ml triethylamine. The mixture was refluxed for 4 hours followed by overnight stirring at room temperature. The precipitated solid was sonicated, filtered, washed with cold EtOH and dried under vacuum to give Zn[(E)-2-(1-(4-(2-methoxyethoxy)pyridin-2-yl)ethylidene)-N,N-dimethylhydrazine-1-carbothioamide]$_2$ (ZN-8) (1.14 g, 95% yield) as a yellow solid in high purity as determined by NMR. $^1$H NMR (400 MHz, DMSO-d6) δ 7.53 (d, J=5.9 Hz, 1H), 7.22 (d, J=2.3 Hz, 1H), 6.85 (dd, J=6.0, 2.4 Hz, 1H), 4.26-4.18 (m, 2H), 3.67-3.61 (m, 2H), 3.28 (s, 3H), 3.22 (s, 6H), 2.54 (s, 3H). MS: 654.60, 656.00, 657.20, 658.40, 660.50 [M+H]$^+$.

Example 2

Synthesis of Complex (ZN-9)

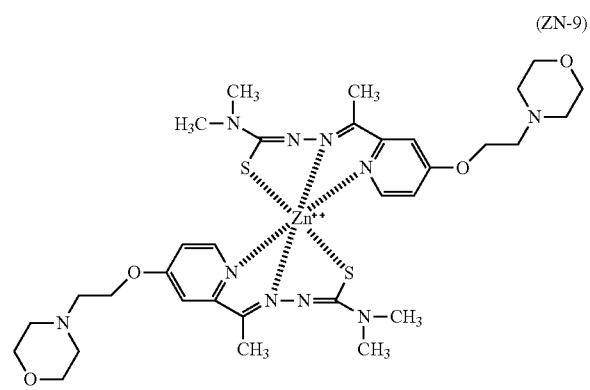

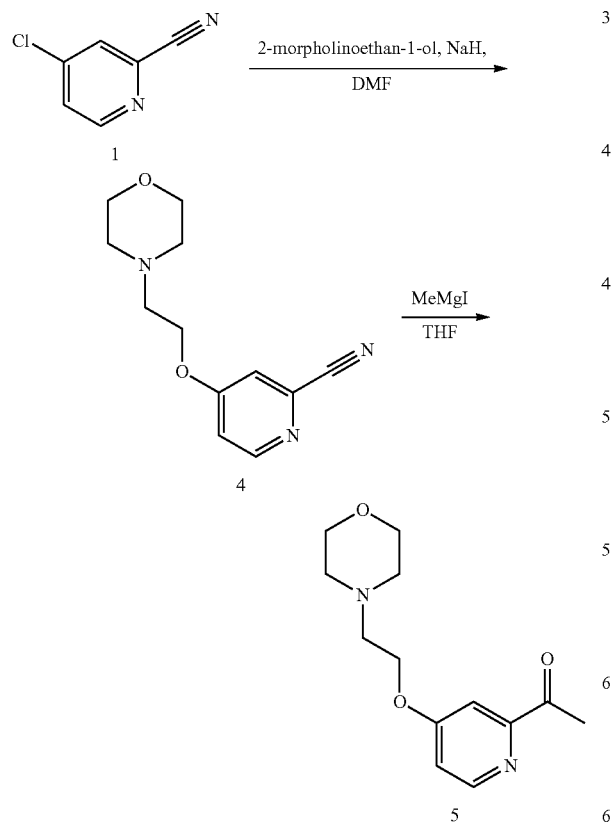

a. Preparation of 4-(2-morpholinoethoxy)picolinonitrile (4)

As described for the synthesis of (2), 4-chloropicolinonitrile (1) and 2-morpholino-1-ol were reacted to give 4-(2-morpholinoethoxy)picolinonitrile (4) (1.59 g, 100% purity by TLC) which was isolated as a beige solid after crystallization from EtOAc/Hex. MS: 234.15 [M+H]$^+$.

b. Preparation of 1-(4-(2-morpholinoethoxy)pyridin-2-yl)ethan-1-one (5)

As described for the synthesis of (3), 4-(2-morpholinoethoxy)picolinonitrile (4) was converted to 1-(4-(2-morpholinoethoxy)pyridin-2-yl)ethan-1-one (5) (1.35 g, 95% purity by LC/MS) and isolated as a yellow oil after purification be silica gel chromatography (50%→100% EtOAc/Hex). MS: 250.70 [M+H]$^+$.

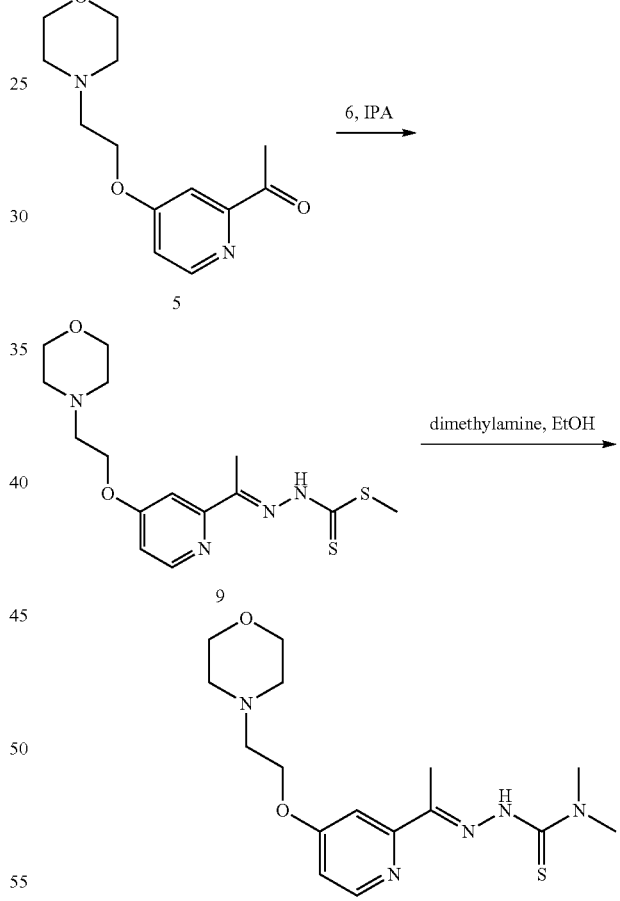

c. Preparation of methyl (E)-2-(1-(4-(2-morpholinoethoxy)pyridin-2-yl)ethylidene)hydrazine-1-carbodithioate (9)

Following the procedure for the synthesis of (7), methyl (E)-2-(1-(4-(2-morpholinoethoxy)pyridin-2-yl)ethylidene)hydrazine-1-carbodithioate (9) (1.08 g, 99% purity by LC/MS) was synthesized from (5) (2.16 g, 7.2 mmol) and isolated as a light yellow solid. MS: 355.10 [M+H]+, MS: 376.70 [M+Na]+.

d. Preparation of (E)-N,N-dimethyl-2-(1-(4-(2-morpholinoethoxy)pyridin-2-yl)ethylidene)hydrazine-1-carbothioamide (10)

Following the procedure for the synthesis of (8), (E)-N,N-dimethyl-2-(1-(4-(2-morpholinoethoxy)pyridin-2-yl)ethylidene)hydrazine-1-carbothioamide (10) (1.24 g, 100% purity by LC/MS) was synthesized from (9) (1.95 g, 5.5 mmol) as a yellow solid. $^1$H NMR (400 MHz, DMSO-d6) δ 9.57 (s, 1H), 8.58-8.37 (m, 1H), 7.51-7.24 (m, 1H), 7.09-6.98 (m, 1H), 4.22 (dt, J=32.6, 5.5 Hz, 2H), 3.61-3.51 (m, 4H), 3.29 (m, 6H), 2.75-2.66 (m, 2H), 2.60 (s, 1H), 2.44 (m, 4H), 2.34 (m, 2H), Note: Peaks have complex splitting from multiple conformational isomers. MS: 351.90 [M+H]+, MS: 373.80 [M+Na]+.

e. Preparation of Zn[(E)-N,N-dimethyl-2-(1-(4-(2-morpholinoethoxy)pyridin-2-yl)ethylidene)hydrazine-1-carbothioamide]$_2$ (ZN-9)

To a suspension of (E)-N,N-dimethyl-2-(1-(4-(2-morpholinoethoxy)pyridin-2-yl)ethylidene)hydrazine-1-carbothioamide (10) (1.13 g, 3.22 mmol, 1 eq) and zinc chloride (219 mg, 1.61 mmol, 0.5 eq) in 30 ml EtOH was added 2 ml triethylamine. The mixture was refluxed for 4 hours followed by overnight stirring at room temperature. The precipitated solid was sonicated, filtered, washed with cold EtOH and dried under vacuum to give Zn[(E)-N,N-dimethyl-2-(1-(4-(2-morpholinoethoxy)pyridin-2-yl)ethylidene)hydrazine-1-carbothioamide]$_2$ (ZN-9) (1.14 g, 92% yield) as a yellow solid in high purity as determined by NMR. $^1$H NMR (400 MHz, DMSO-d6) δ 7.52 (d, J=5.9 Hz, 1H), 7.21 (d, J=2.3 Hz, 1H), 6.85 (dd, J=6.0, 2.4 Hz, 1H), 4.20 (t, J=5.6 Hz, 2H), 3.57-3.50 (t, J=4.6 Hz, 4H), 3.22 (s, 6H), 2.67 (t, J=5.6 Hz, 2H), 2.54 (s, 3H), 2.43 (t, J=4.7 Hz, 4H). MS: 764.80, 766.05, 767.45, 769.10, 770,35 [M+H]+.

Example 3

Synthesis of Zn[(E)-N,N-dimethyl-2-(1-(4-(2-morpholinoethoxy)pyridin-2-yl)ethylidene)hydrazine-1-carbothioamide]$_2$ bis mesylate salt (ZN-9 Mesylate Salt)

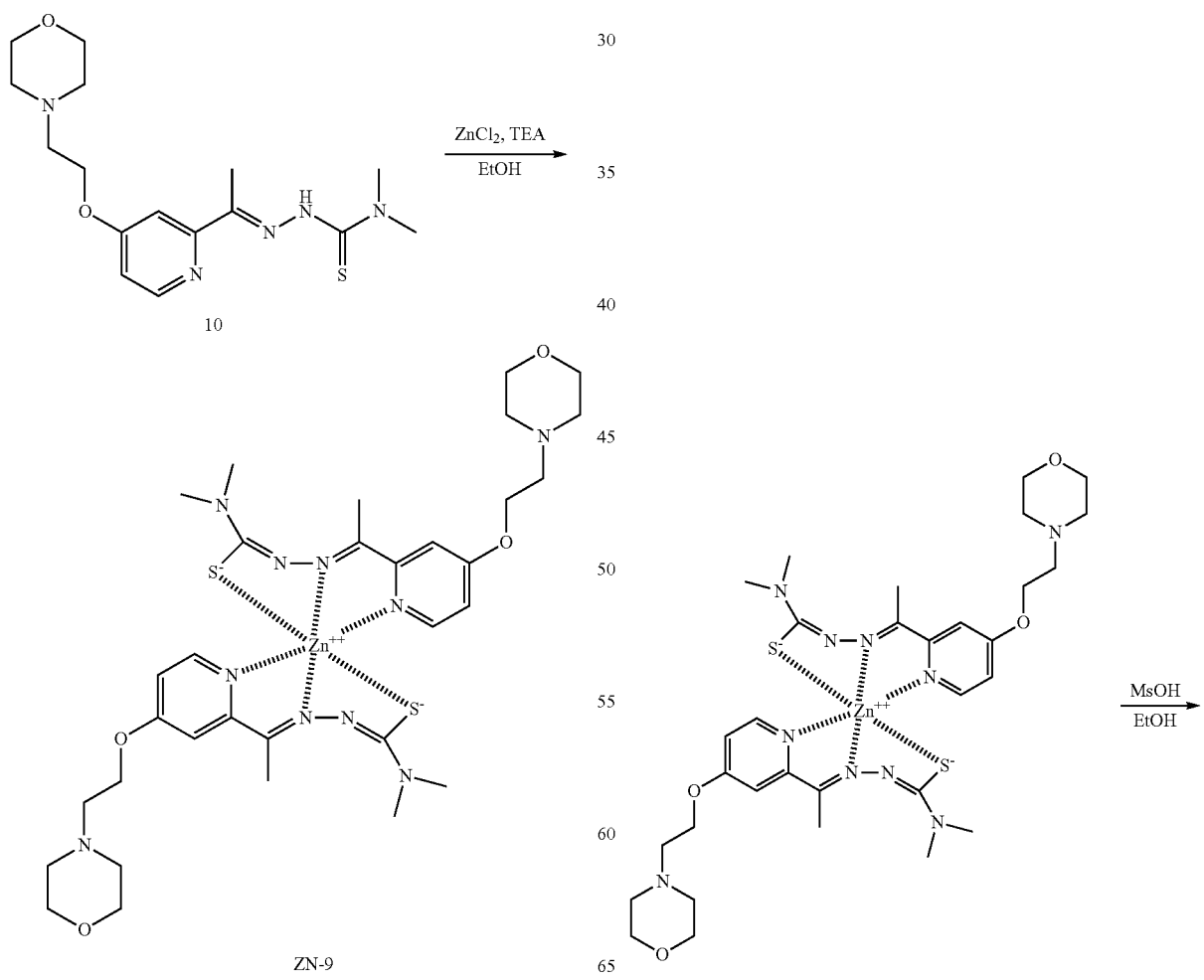

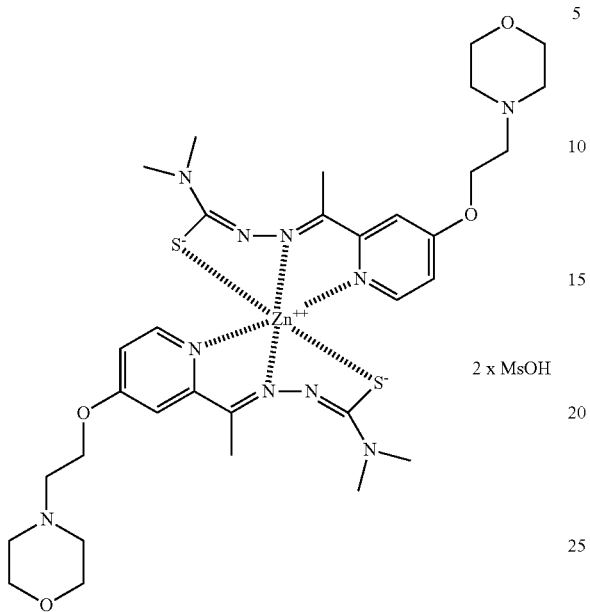

ZN-9 Mesylate Salt 2 x MsOH

Zn[(E)-N,N-dimethyl-2-(1-(4-(2-morpholinoethoxy)pyridin-2-yl)ethylidene)-hydrazine-1-carbothioamide]₂ (ZN-9) (500 mg, 0.65 mmol, 1 eq) was dissolved in 200 ml ethanol with gentle heating. A stock solution of mesic acid was prepared by dissolution of methanesulfonic acid (500 uL) in 19.5 ml ethanol. Mesic acid stock solution (3.4 ml, 1.30 mmol, 2 eq) was added to the solution of zinc complex in ethanol. After stirring for 30 minutes at room temperature, the solution was concentrated under reduced pressure to 25 ml. To this concentrated solution was added roughly 25 ml diethyl ether. A yellow solid precipitated from solution that was sonicated, filtered and dried under vacuum to afford Zn[(E)-N,N-dimethyl-2-(1-(4-(2-morpholinoethoxy)pyridin-2-yl)ethylidene)hydrazine-1-carbothioamide]₂ bis mesylate salt (ZN-9 Mesylate salt) (603 mg, 96% yield) in high purity as determined by NMR. ¹H NMR (400 MHz, DMSO-d6) δ 9.86 (s, 2H), 7.59 (s, 2H), 7.25 (s, 2H), 6.90 (s, 2H), 4.49 (s, 4H), 3.97 (d, J=12.8 Hz, 4H), 3.77-3.41 (m, 16H), 3.23 (s, 12H), 2.59-2.54 (s, 6H), 2.31 (s, 6H). MS: 765.00, 766.90, 768.90, 770.75 [M+H]⁺.

Example 4

Synthesis of Zn[(E)-N'-(1-(4-(2-methoxyethoxy)pyridin-2-yl)ethylidene)azetidine-1-carbothiohydrazide]₂ (ZN-10)

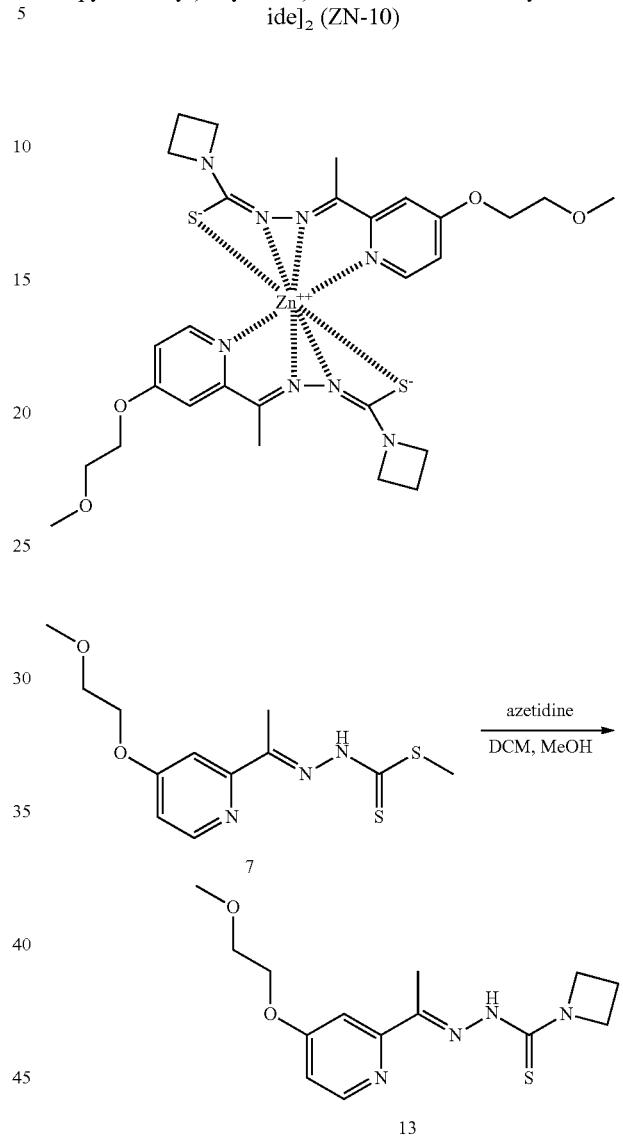

a. (E)-N'-(1-(4-(2-methoxyethoxy)pyridin-2-yl)ethylidene)azetidine-1-carbothiohydrazide (13)

To a solution of methyl (E)-2-(1-(4-(2-methoxyethoxy)pyridin-2-yl)ethylidene)hydrazine-1-carbodithioate (7) (265 mg, 0.89 mmol) in 5 mL DCM and 5 mL MeOH was added azetidine (239 μL, 3.54 mmol, 4.0 eq). After stirring overnight at room temperature, the reaction was determined complete by LC/MS and concentrated under reduced pressure. The crude product was purified by silica gel chromatography (0%→2% MeOH/DCM) and concentrated under reduced pressure. The concentrate was recrystallized from EtOAc, sonicated, filtered and dried under vacuum to afford (E)-N'-(1-(4-(2-methoxyethoxy)pyridin-2-yl)ethylidene)azetidine-1-carbothiohydrazide (13) (204 mg, 99% purity) as a yellow solid. ¹H NMR (500 MHz, DMSO-d₆) δ 10.22 (s, 1H), 8.39 (dd, J=5.7, 0.5 Hz, 1H), 7.38 (d, J=2.3 Hz, 1H), 7.00 (dd, J=5.7, 2.5 Hz, 1H), 4.60 (s, 2H), 4.25-4.19 (m, 2H), 3.72-3.63 (m, 2H), 3.30 (s, 3H), 2.33 (s, 3H), 2.29-2.21 (m, 2H). MS: 309.05 [M+H]⁺.

Example 5

Synthesis of Zn[(E)-2-(1-(4-(2-methoxypyridin-2-yl)ethylidene)-N,N-dimethylhydrazine-1-carbothioamide]₂ (ZN-11)

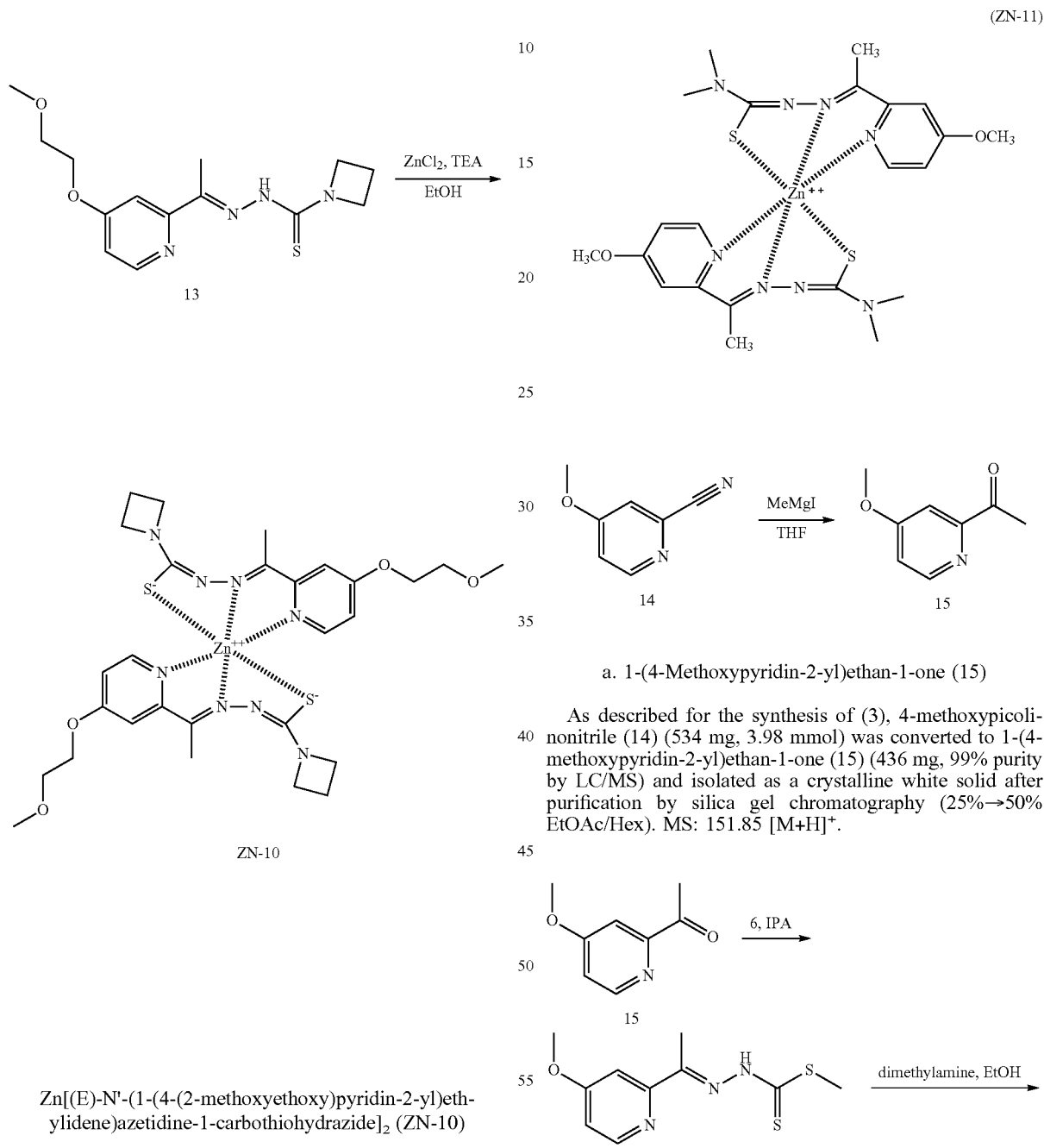

Zn[(E)-N'-(1-(4-(2-methoxyethoxy)pyridin-2-yl)ethylidene)azetidine-1-carbothiohydrazide]₂ (ZN-10)

Following the procedure for the synthesis of (ZN-8), the title compound (ZN-10) (199 mg) was synthesized from (E)-N'-(1-(4-(2-methoxyethoxy)pyridin-2-yl)ethylidene)azetidine-1-carbothiohydrazide (13) (197 mg, 0.639 mmol) and isolated as a bright yellow solid. ¹H NMR (500 MHz, DMSO-d₆) δ 7.52 (d, J=5.9 Hz, 1H), 7.20 (d, J=2.4 Hz, 1H), 6.87 (dd, J=5.9, 2.4 Hz, 1H), 4.30-4.17 (m, 2H), 4.01 (m, 4H), 3.71-3.60 (m, 2H), 3.28 (s, 3H), 2.51 (s, 3H), 2.23 (p, J=7.5 Hz, 2H).

a. 1-(4-Methoxypyridin-2-yl)ethan-1-one (15)

As described for the synthesis of (3), 4-methoxypicolinonitrile (14) (534 mg, 3.98 mmol) was converted to 1-(4-methoxypyridin-2-yl)ethan-1-one (15) (436 mg, 99% purity by LC/MS) and isolated as a crystalline white solid after purification by silica gel chromatography (25%→50% EtOAc/Hex). MS: 151.85 [M+H]⁺.

b. Methyl (E)-2-(1-(4-methoxypyridin-2-yl)ethylidene)hydrazine-1-carbodithioate (16)

Following the procedure for the synthesis of (7), using methyl (E)-methoxypyridin-2-yl)ethylidene)hydrazine-1-carbodithioate (15) (252 mg, 1.67 mmol), the title compound (16) (391 mg, 100% purity by LC/MS) was isolated as an orange solid. MS: 256.75 [M+H]$^+$.

c. (E)-2-(1-(4-methoxypyridin-2-yl)ethylidene)-N,N-dimethylhydrazine-1-carbothioamide (17)

Following the procedure for the synthesis of (8), (E)-2-(1-(4-methoxypyridin-2-yl)ethylidene)-N,N-dimethylhydrazine-1-carbothioamide (17) (299 mg, 98% purity by LC/MS) was synthesized from (9) (391 mg, 1.53 mmol) and isolated as a yellow solid, $^1$H NMR (500 MHz, DMSO-d$_6$) δ 9.60 (s, 1H), 8.61-8.40 (m, 1H), 7.54-7.25 (m, 1H), 7.18-6.99 (m, 1H), 3.94-3.85 (m, 3H), 2.62-2.36 (m, 3H). Note: Peaks have complex splitting from multiple conformational isomers. MS: 252.85 [M+H]$^+$.

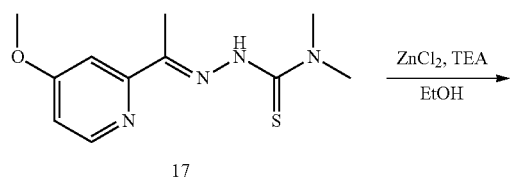

17

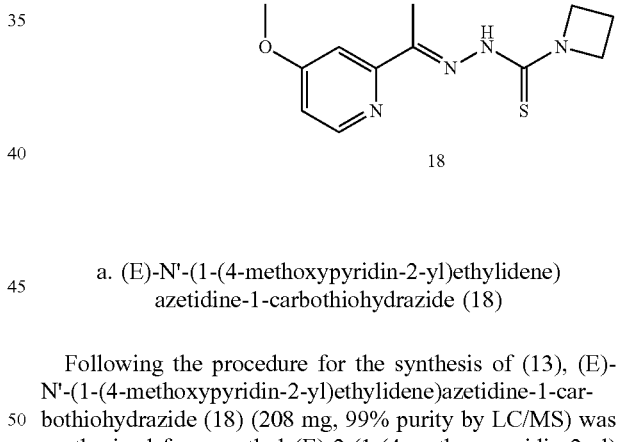

ZN-11 d. Zn[(E)-2-(1-(4-methoxypyridin-2-yl)ethylidene)-N,N-dimethylhydrazine-1-carbothioamide]$_2$ (ZN-11)

Following the procedure for the synthesis of (ZN-8), the title compound (ZN-11) (277.3 mg) was synthesized from (E)-2-(1-(4-methoxypyridin-2-yl)ethylidene)-N,N-dimethylhydrazine-1-carbothioamide (17) (249 mg, 0.987 mmol) and isolated as a bright yellow solid. $^1$H NMR (500 MHz, DMSO-d$_6$) δ 7.53 (d, J=5.9 Hz, 1H), 7.18 (d, J=2.4 Hz, 1H), 6.83 (dd, J=5.9, 2.4 Hz, 1H), 3.83 (s, 3H), 3.20 (s, 6H), 2.53 (s, 3H).

Example 6

Synthesis of Zn[(E)-N'-(1-(4-methoxypyridin-2-yl)ethylidene)azetidine-1-carbothiohydrazide]$_2$ (ZN-13)

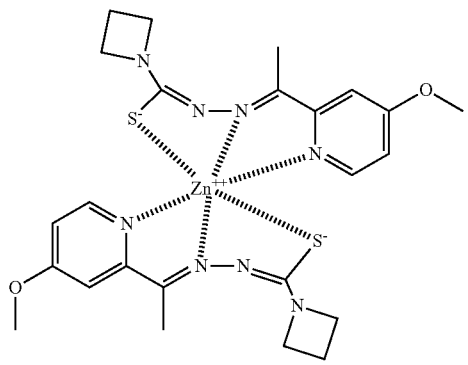

ZN-13

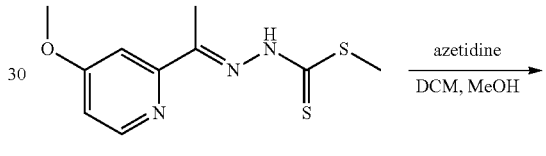

16

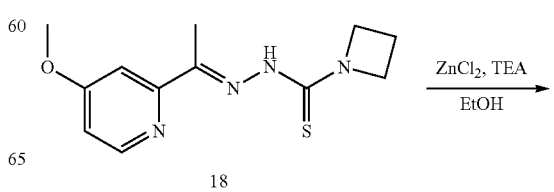

18 a. (E)-N'-(1-(4-methoxypyridin-2-yl)ethylidene)azetidine-1-carbothiohydrazide (18)

Following the procedure for the synthesis of (13), (E)-N'-(1-(4-methoxypyridin-2-yl)ethylidene)azetidine-1-carbothiohydrazide (18) (208 mg, 99% purity by LC/MS) was synthesized from methyl (E)-2-(1-(4-methoxypyridin-2-yl)ethylidene)hydrazine-1-carbodithioate (16) (367 mg, 1.44 mmol) and isolated as a pale yellow solid. $^1$H NMR (500 MHz, DMSO-d$_6$) δ 10.24 (s, 1H), 8.41 (dd, J=5.7, 0.5 Hz, 1H), 7.40 (d, J=2.6 Hz, 1H), 6.99 (dd, J=5.7, 2.6 Hz. 1H), 4.61 (s, 2H), 4.12 (s, 2H), 3.85 (s, 3H), 2.33 (s, 3H), 2.29-2.22 (m, 2H). MS: 286.85 [M+Na]$^+$.

18 b. Zn[(E)-N'-(1-(4-methoxypyridin-2-yl)ethylidene)azetidine-1-carbothiohydrazide]₂ (ZN-13)

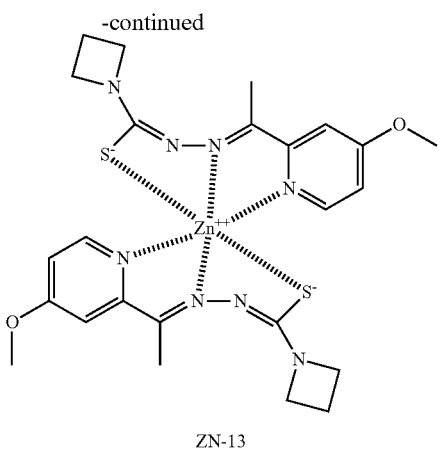

ZN-13

Following the procedure for the synthesis of (ZN-8), the title compound (ZN-13) (215 mg) was synthesized from (E)-N'-(1-(4-methoxypyridin-2-yl)ethylidene)azetidine-carbothiohydrazide (18) (190 mg, 0.719 mmol) and isolated as a bright yellow solid. ¹H NMR (500 MHz, DMSO-d₆) δ 7.53 (d, J=5.9 Hz, 1H), 7.19 (d, J=2.4 Hz, 1H), 6.86 (dd, J=5.9, 2.4 Hz, 1H), 4.04 (s, 4H), 3.85 (s, 3H), 2.53 (s, 3H), 2.23 (p, J=7.5 Hz, 2H).

Example 7

Synthesis of Zn[(S,E)-N,N-dimethyl-2-(1-(4-((tetrahydrofuran-3-yl)oxy)pyridin-2-yl)ethylidene)hydrazine-1-carbothioamide]₂ (ZN-14)

Zn-14

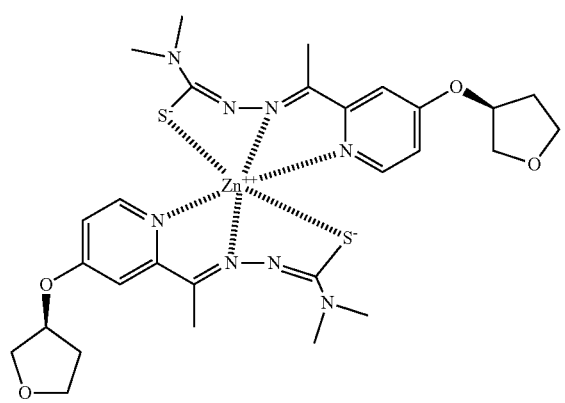

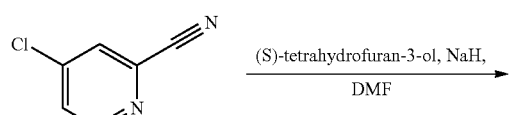

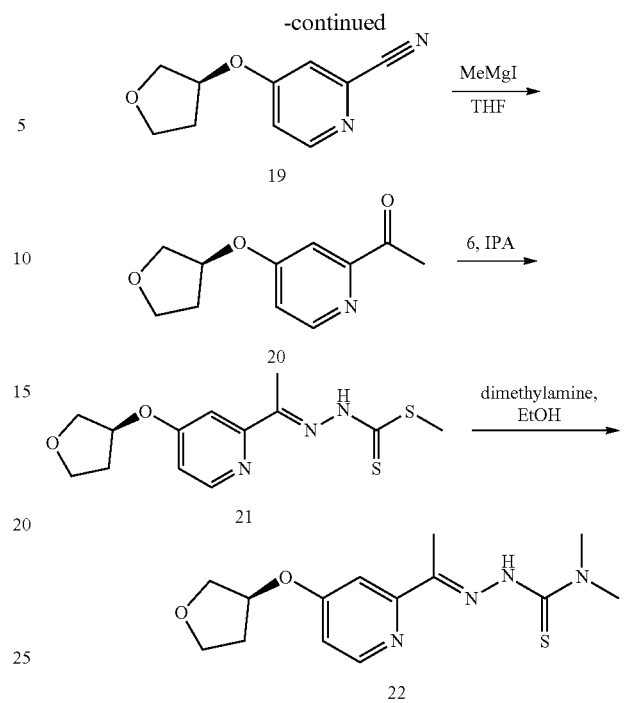

a. (S)-4-((Tetrahydrofuran-3-yl)oxy)picolinonitrile (19)

As described for the synthesis of (2), 4-chloropicolinonitrile (1) (1.0 g, 7.2 mmol) and (S)-tetrahydrofuran-3-ol were reacted to give (S)-4-((tetrahydrofuran-3-yl)oxy)picolinonitrile (19) (577 mg, 3.0 mmol, 42% yield, 100% purity by LCMS) which was isolated as a yellow oil after purification be silica gel chromatography (25%→50% EtOAc/Hex). MS: 190.9 [M+H]⁺.

b. (S)-1-(4-((Tetrahydrofuran-3-yl)oxy)pyridin-2-yl)ethan-1-one (20)

As described for the synthesis of (3), (S)-4-((tetrahydrofuran-3-yl)oxy)picolinonitrile (19) (550 mg, 2.9 mmol) was converted to (5)-1-(4-((tetrahydrofuran-3-yl)oxy)pyridin-2-yl)ethan-1-one (20) (487 mg, 2.35 mmol, 81% yield, 97% purity by LC/MS,) and isolated as a yellow oil after purification be silica gel chromatography (25%→50% EtOAc/Hex). MS: 207.55 [M+H]⁺.

c. Methyl (S,E)-2-(1-(4-((tetrahydrofuran-3-yl)oxy)pyridin-2-yl)ethylidene)-hydrazine-1-carbodithioate (21)

Following the procedure for the synthesis of (7), methyl (S,E)-2-(1-(4-((tetrahydrofuran-3-yl)oxy)pyridin-2-yl)ethylidene)hydrazine-1-carbodithioate (21) (96% purity by LC/MS) was synthesized from (20) (400 mg, 1.93 mmol) and isolated as a yellow solid after filtration that was used in next step without determining yield. MS: 311.9 [M+H]⁺.

d. (S,E)-N,N-Dimethyl-2-(1-(4-((tetrahydrofuran-3-yl)oxy)pyridin-2-yl)ethylidene)hydrazine-1-carbothioamide (22)

Following the procedure for the synthesis of (8), (S,E)-N,N-dimethyl-2-(1-(4-((tetrahydrofuran-3-yl)oxy)pyridin- 2-yl)ethylidene)hydrazine-1-carbothioamide (22) (117 mg, 0.380 mmol, 20% yield over 2 steps, 100% purity by LC/MS) was synthesized from (21) and isolated as a yellow solid after purification by silica gel chromatography (0%→2% MeOH/DCM) and recrystallization from EtOAc. $^1$H NMR (500 MHz, DMSO-$d_6$) δ 9.68-9.52 (s, 1H), 8.46 (m, J=67.0, 5.6 Hz, 1H), 7.57-6.93 (m, 2H), 5.21 (d, J=65.7 Hz, 1H), 3.97-3.70 (m, 4H), 3.38-3.25 (m, 6H), 2.62 (s, 1H), 2.41-2.18 (m, 3H), 1.98 (s, 1H). Note: Peaks have complex splitting from multiple conformational isomers. MS: 308.9 [M+H]$^+$.

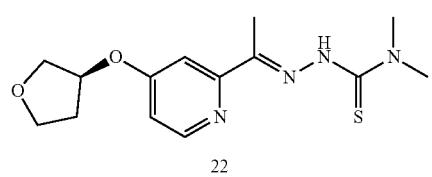

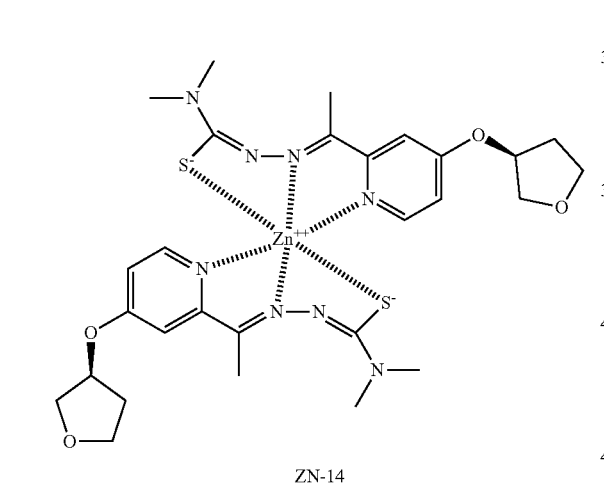

ZN-14 e. Zn[(S,E)-N,N-dimethyl-2-(1-(4-((tetrahydrofuran-3-yl)oxy)pyridin-2-yl)ethylidene)hydrazine-1-carbothioamide]$_2$ (ZN-14)

Following the procedure for the synthesis of (ZN-8), the title compound (ZN-14) (111 mg) was synthesized from ((S,E)-N,N-dimethyl-2-(1-(4-((tetrahydrofuran-3-yl)oxy)pyridin-2-yl)ethylidene)hydrazine-1-carbothioamide (22) (103 mg, 0.334 mmol) and isolated as a bright yellow solid after filtration. $^1$H NMR (500 MHz, DMSO-$d_6$) δ 7.55 (d, J=5.9 Hz, 1H), 7.17 (d, J=2.3 Hz, 1H), 6.86 (dd, J=5.9, 2.3 Hz, 1H), 5.17 (ddt, J=6.0, 4.3, 1.7 Hz, 1H), 3.92-3.70 (m, 4H), 3.22 (s, 6H), 2.53 (s, 3H), 2.25 (tq, J=14.4, 8.0, 7.2 Hz, 1H), 1.99-1.84 (m, 1H).

Example 8

Synthesis of Zn[(S,E)-N,N-dimethyl-2-(1-(5-((tetrahydrofuran-3-yl)oxy)pyridin-2-yl)ethylidene)hydrazine-1-carbothioamide]$_2$ (ZN-15)

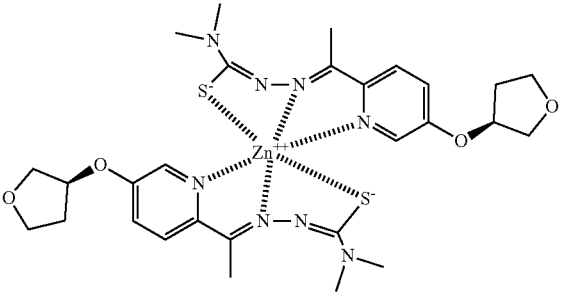

Zn-15

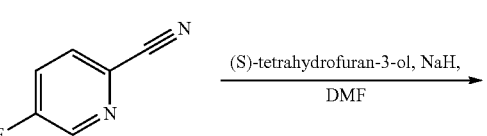

23

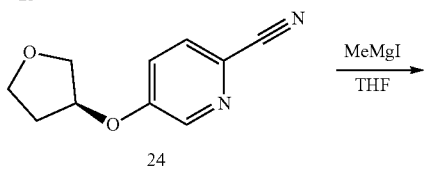

24

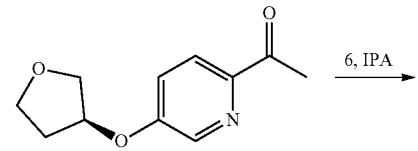

25

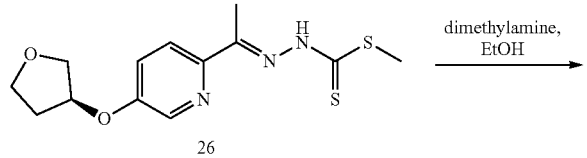

26

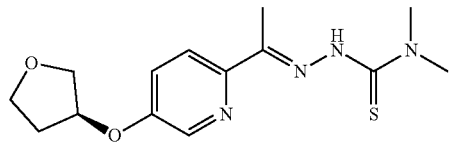

27 a. (S)-5-((Tetrahydrofuran-3-yl)oxy)picolinonitrile (24)

As described for the synthesis of (2), 5-fluoropicolinonitrile (23) (1.0 g, 8.2 mmol) and 2-morpholino-1-ol were reacted to give (5)-5-((tetrahydrofuran-3-yl)oxy)picolinonitrile (24) (1.34 g, 7.0 mmol, 85% yield, 100% purity by LC/MS) which was isolated as a light yellow oil after purification be silica gel chromatography (25%→50% EtOAc/Hex). MS: 190.9 [M+H]⁺.

b. (S)-1-(5-((Tetrahydrofuran-3-yl)oxy)pyridin-2-yl)ethan-1-one (25)

As described for the synthesis of (3), (S)-5-((tetrahydrofuran-3-yl)oxy)picolinonitrile (24) (550 mg, 2.9 mmol) was converted to (S)-1-(5-((tetrahydrofuran-3-yl)oxy)pyridin-2-yl)ethan-1-one (25) (445 mg, 95% purity by LC/MS) and isolated as a yellow oil after purification be silica gel chromatography (25%→50% EtOAc/Hex). MS: 208.0 [M+H]⁺.

c. Methyl (S,E)-2-(1-(5-((tetrahydrofuran-3-yl)oxy)pyridin-2-yl)ethylidene)-hydrazine-1-carbodithioate (26)

Following the procedure for the synthesis of (7), methyl (S,E)-2-(1-(5-((tetrahydrofuran-3-yl)oxy)pyridin-2-yl)ethylidene)hydrazine-1-carbodithioate (26) (99% purity by LC/MS) was synthesized from (25) (400 mg, 1.93 mmol) and isolated as a light yellow solid after filtration that was used in next step without determining yield. MS: 311.9 [M+H]⁺.

d. (S,E)-N,N-Dimethyl-2-(1-(5-((tetrahydrofuran-3-yl)oxy)pyridin-2-yl)ethylidene)-hydrazine-1-carbothioamide (27)

Following the procedure for the synthesis of (8), (S,E)-N,N-dimethyl-2-(1-(5-((tetrahydrofuran-3-yl)oxy)pyridin-2-yl)ethylidene)hydrazine-1-carbothioamide (27) (179 mg, 0.58 mmol, 30% yield over 2 steps, 100% purity by LC/MS) was synthesized from (26) and isolated as a yellow solid after purification by silica gel chromatography (0%→2% MeOH/DCM) and recrystallization from EtOAc. ¹H NMR (500 MHz, DMSO-d₆) δ 9.50 (s, 1H), 8.53-8.21 (m, 1H), 8.02-7.72 (m, 1H), 7.48 (ddd, J=62.3, 8.8, 2.9 Hz, 1H), 5.27-5.10 (m, 1H), 3.95-3.70 (m, 4H), 3.32-3.29 (m, 4H), 3.27-3.19 (m, 2H), 2.60 (d, J=1.2 Hz, 1H), 2.38-2.19 (m, 3H), 1.97 (ddd, J=13.5, 10.9, 5.9 Hz, 1H). Note: Peaks have complex splitting from multiple conformational isomers. MS: 308.9 [M+H]⁺.

e. Zn[(S)-N,N-Dimethyl-2-(1,-(5-((tetrahydrofuran-3-yl)oxy)pyridin-2-yl)ethylidene)hydrazine-4-carbothioamide]₂ (ZN-15)

Following the procedure for the synthesis of (ZN-8), the title compound (ZN-15) (106 mg) was synthesized from (S,E)-N,N-dimethyl-2-(1-(5-((tetrahydrofuran-3-yl)oxy)pyridin-2-yl)ethylidene)hydrazine-1-carbothioamide (27) (101 mg, 0.328 mmol) and isolated as a bright yellow solid after filtration. ¹H NMR (500 MHz, DMSO-d₆) δ 7.71 (d, J=8.8 Hz, 1H), 7.48 (ddd, J=8.9, 2.9, 1.41 Hz, 1H), 7.37-7.32 (m, 1H), 4.95 (dtd, J=6.2, 4.0, 1.61 Hz, 1H), 3.84-3.66 (m, 4H), 3.21 (d, J=1.1 Hz, 6H), 2.57 (s, 3H), 2.26-2.12 (m, 1H), 1.95-1.78 (m, 1H).

Example 9

Solubility of Zinc Complexes

Results of solubility measurements for zinc complexes are shown in the following Table.

| | Solubility Data | | | | | |
|---|---|---|---|---|---|---|
| | DMSO 10 mg/ml | DMSO 4 mg/ml | H₂O:DMSO 1:1 0.5 mg/mL | EtOH 2 mg/ml | EtOH 1 mg/ml | 0.9% Saline |
| ZMC-1 | No | Yes (3 mg/ml) | No | ND | ND | ND |
| ZN-1 | No | Yes | No | No | No | ND |
| ZN-8 | Yes | Yes | No | Partial | YES | ND |
| ZN-9 | Yes | ND | ND | Yes | NO | ND |
| ZN-9 Mesylate salt | ND | ND | ND | ND | ND | 5-10 mg/ml |
| Zn-11 | Yes | Yes | No at 0.5 mg/mL* | ND | Partial | ND |
| Zn-14 | Yes | Yes | No at 0.5 mg/mL# | ND | Partial | ND |

*Qualitatively slightly more soluble compared with Zn-8 and Zn-14
Qualitatively the least soluble compared with Zn-11 and Zn-8
ND (not determined)

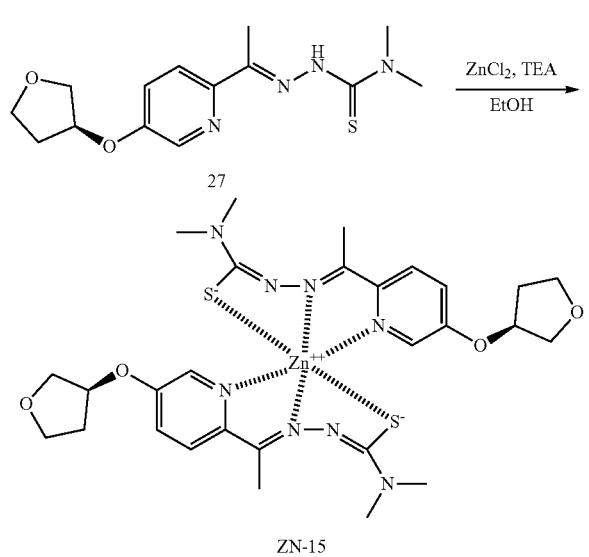

ZN-15

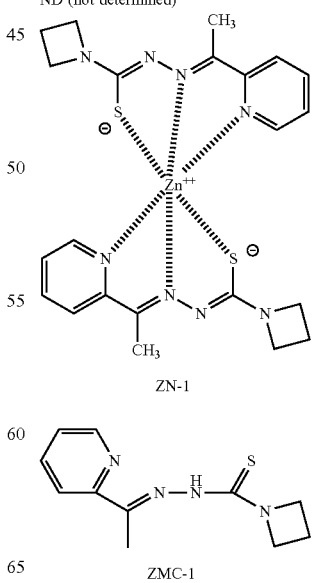

ZN-1

ZMC-1

Example 10

Cell Based Assays

An immunofluorescent staining using p53 conformation specific antibodies is used to determine if a test compound could induce the mutant p53 protein refolding to a wildtype conformation. The p53-R175H cells (e.g. TOV112D) cultured in DMEM+10% FBS are treated with a test compound for 6 hours, then fixed and stained with the antibodies PAB1620 (recognizing WT conformation) and PAB240 (recognizing misfolded/unfolded conformation) respectively.

Cell growth inhibition assay using human tumor cell lines with different p53 status (wildtype, null, p53-R175H or other zinc binding deficient mutants) are employed to determine if a test compound functions as a zinc metallochaperone to restore wildtype p53 functions. Five thousand cells per well are cultured in 96-well plate to reach the 50% confluence on the second day when treated with serial dilutions of the compounds. Growth is measured by Calcein AM assay after incubation for 72 hours.

Example 11

In Vivo Assays

Mice are housed and treated according to guidelines and all the mouse experiments are done with the approval of institutional Animal Care and Use Committee (IACUC). For Maximum tolerated dose assays, 8-12 week old mice (5 mice per dose) are administered by intraperitoneal injection (IP) daily with various doses for 14 days and health, behavior and body weight are monitored. Human cancer cell lines and mouse tumor cell lines are implanted into the nude mice (NCR nu/nu) for Xenograft tumor assays. Tumor dimensions are measured every other day and their volumes are calculated by length (L) and width (W) using the formula: volume=L×W$^2$×π/6. Tumors over 50 mm$^3$ are treated by daily administration of a test compound by intravenous injection (IV) or IP. Genetically engineered transgenic KPC mice (Pdx1-CRE; KRas$^{G12D/+}$; p53$^{R17H/+}$ and Pdx1-CRE; KRas$^{G12D/+}$; p53$^{R270H/+}$) are administered a test compound by IP daily. The survival and the tumor growth rate represent the efficacy of a test compound. The endogenous tumor growth is monitored with ultrasound by VisualSonics Vevo 3100.

Example 12

Cell Growth Inhibition Assay

The cell growth inhibition assay was performed by Calcein AM assay (Trevigen). Five thousand cells per well were cultured in 96-well plate to reach the 50% confluence on the second day when treated with serial dilutions of the compounds. Growth was measured by Calcein AM assay (Trevigen) and Victor Plate reader instrument (PerkinElmer) after incubation for 3 days. EC$_{50S}$ were compared to Zn-1 for efficacy. Results are shown in the following table.

| EC$_{50}$s of Zn-8, Zn-9, Zn-10-11 and Zn-14, compared with Zn-1 | | |
|---|---|---|
| | EC$_{50}$ (nM) | Fold (compound/Zn-1) | Fold (Zn-1/compound) |
| Zn-1 | 2.69 | 1.0 | 1.0 |
| Zn-8 | 0.37 | 0.1 | 7.3 |
| Zn-9 | 18.09 | 6.7 | 0.1 |
| Zn-10 | 1.15 | 0.4 | 2.3 |
| Zn-11 | 0.22 | 0.1 | 12.2 |
| Zn-14 | 0.69 | 0.3 | 3.9 |
| Zn-15 | 7.08 | 0.4 | 2.6 |

Example 13

Additional Studies

Zn-8, Zn-11 and Zn-14 are at least 3× more soluble in DMSO than Zn-1. Zn-11 was qualitatively more soluble in 1:1 DMSO:water at 0.5 mg/mL than Zn-8 and Zn-14. Initial characterization studies showed that Zn-8, Zn-11 and Zn-14 are 14-fold 209-fold and 28-fold respectively more potent than the monomer from Zn-1 against p53R175H cells in vitro, whereas Zn-1 is only 3-fold more potent than the same monomer. Using p53 conformation specific antibodies, Zn-8, like Zn-1, induces a wild type conformation change with loss of the mutant specific (PAB240) and gain of the wild type specific (PAB 1620). When Zn-8 was examined for restoration of wild type transcriptional function by quantitative PCR of p53 target genes, markedly induced p21, PUMA and GDF15 levels, like Zn-1, were found. This induction was mutant p53 dependent as these increases were not observed using the same cell line in which the mutant p53R175H was knocked out using CRISPR. To confirm that the cell growth inhibitory properties of Zn-8 were p53 dependent, mutant p53 was knocked down using an siRNA; cell growth inhibition was attenuated by more than a log fold.

Example 14

Safety Screening

The complex ZN-8 was subjected to Safety Screening (www.eurofinsdiscovery services.com/catalogmanagement/viewitem/SafetyScreen44-Panel-Cerep/P270#additionalInfo). The results are provided in the following table.

| ZN-8 CEREP-44 Safety Screen | | | |
|---|---|---|---|
| FAMILY GPCR | ASSAY | FAMILY TRANSPORTER | ASSAY |
| ADENOSINE | A2A | DOPAMINE | dopamine transporter |
| ADRENERGIC | alpha1A | NOREPINEPHRINE | norepinephrine transporter |
| | alpha2A | SEROTONIN | 5-HT transporter |
| | beta1 | ION CHANNELS | |
| | beta2 | GABA CHANNELS | BZD (central) |

-continued

| ZN-8 CEREP-44 Safety Screen | | | |
|---|---|---|---|
| FAMILY GPCR | ASSAY | FAMILY TRANSPORTER | ASSAY |
| CANNABINOID | CB1 | GLUTAMATE CHANNELS | NMDA |
|  | CB2 | NICOTINIC CHANNELS | N neuronal α4β2 |
| CHOLECYSTOKININ | CCK1 (CCKA) | SEROTONIN CHANNELS | 5-HT3 |
| DOPAMINE | D1 | Ca2+ CHANNELS | $Ca^{2+}$ channel (L, dihydropyridine site) |
|  | D2S | K+ CHANNELS | hERG (membrane preparation) |
| ENDOTHELIN | ETA |  | KV channel |
| HISTAMINE | H1 | Na+ CHANNELS | $Na^+$ channel (site 2) |
|  | H2 | NUCLEAR RECEPTORS |  |
| MUSCARINIC | M1 | STEROID NUCLEAR RECEPTOR | AR |
|  |  |  | GR |
|  | M2 | KINASES |  |
|  | M3 | CTK | Lck Kinase |
| OPIOID & OPIOID-LIKE | delta2 (DOP) | OTHER NON-KINASE ENZYMES |  |
|  | kappa (KOP) | AA METABOLISM | COX1 |
|  | mu (MOP) |  | COX2 |
| SEROTONIN | 5-HT1A | MONOAMINE & NEUROTRANSMITTER PHOSPHODIESTERASES | Acetylcholinesterase |
|  | 5-HT1B |  | MOA-A |
|  | 5-HT2A |  | $PDE_3A$ |
|  | 5-HT2B |  | $PDE_4D2$ |
| VASOPRESSIN | V1a |  |  |

The only positive hits were:
COX1(h) 54.8% Inh.@10 mM
COX2(h) 50.7% Inh.@10 mM
5-$HT_{2B}$ 58.7% Inh.@10 mM The following compounds can also be prepared using synthetic procedures described herein above such as the synthesis of compound (8) and complex (ZN-8).

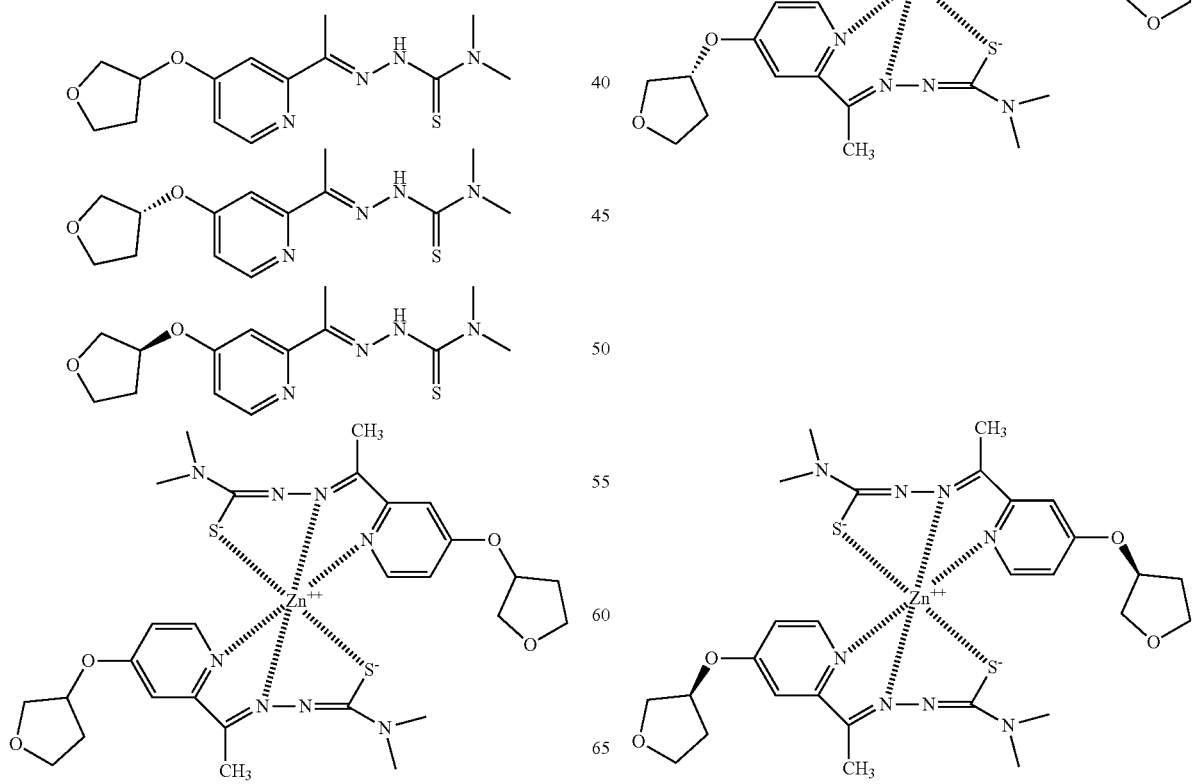

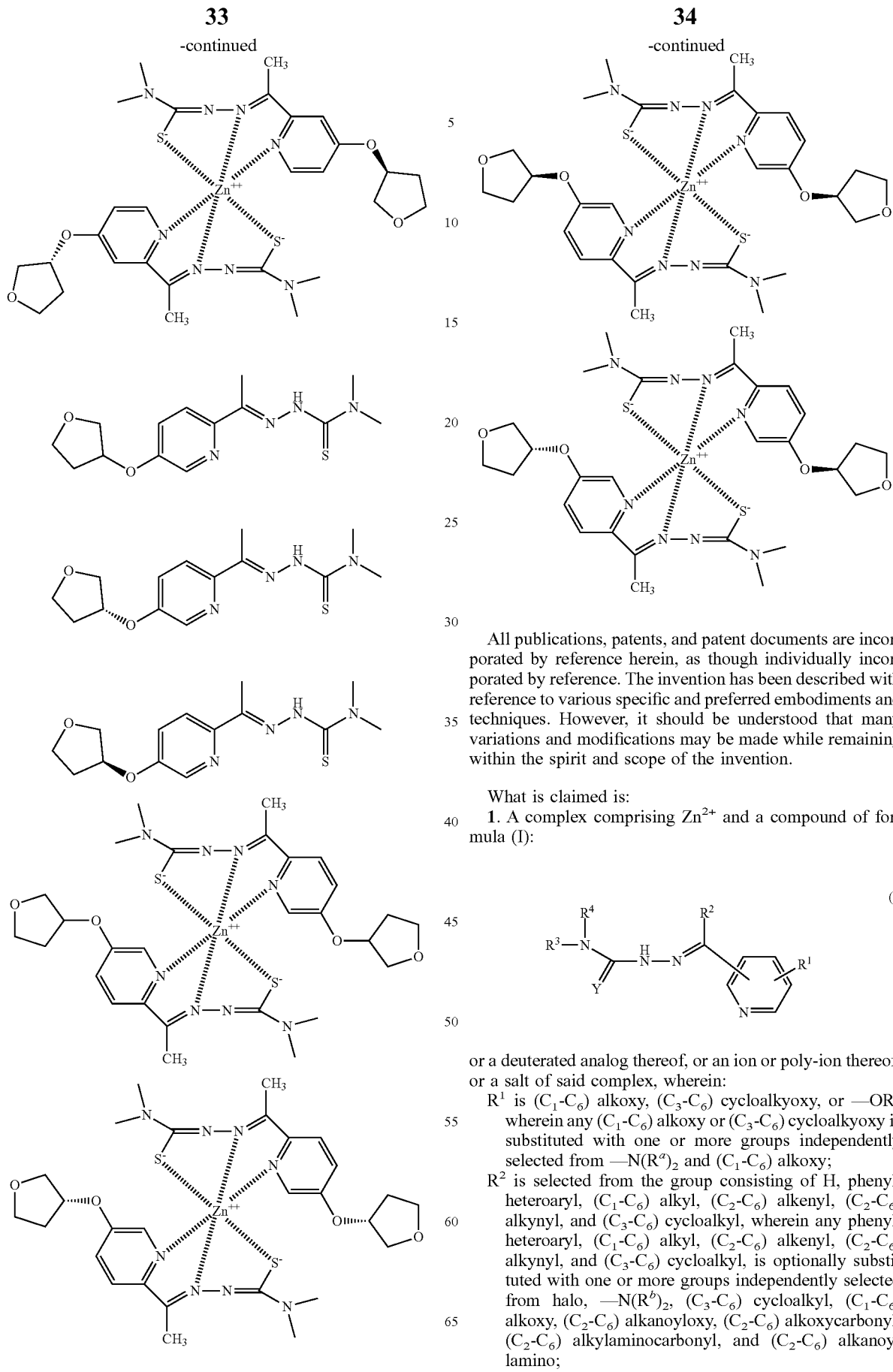

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A complex comprising $Zn^{2+}$ and a compound of formula (I):

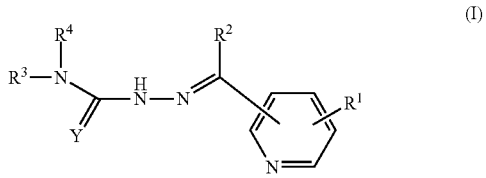

or a deuterated analog thereof, or an ion or poly-ion thereof, or a salt of said complex, wherein:

$R^1$ is $(C_1-C_6)$ alkoxy, $(C_3-C_6)$ cycloalkyoxy, or —$OR^5$ wherein any $(C_1-C_6)$ alkoxy or $(C_3-C_6)$ cycloalkyoxy is substituted with one or more groups independently selected from —$N(R^a)_2$ and $(C_1-C_6)$ alkoxy;

$R^2$ is selected from the group consisting of H, phenyl, heteroaryl, $(C_1-C_6)$ alkyl, $(C_2-C_6)$ alkenyl, $(C_2-C_6)$ alkynyl, and $(C_3-C_6)$ cycloalkyl, wherein any phenyl, heteroaryl, $(C_1-C_6)$ alkyl, $(C_2-C_6)$ alkenyl, $(C_2-C_6)$ alkynyl, and $(C_3-C_6)$ cycloalkyl, is optionally substituted with one or more groups independently selected from halo, —$N(R^b)_2$, $(C_3-C_6)$ cycloalkyl, $(C_1-C_6)$ alkoxy, $(C_2-C_6)$ alkanoyloxy, $(C_2-C_6)$ alkoxycarbonyl, $(C_2-C_6)$ alkylaminocarbonyl, and $(C_2-C_6)$ alkanoylamino;

R³ and R⁴ are each independently selected from H, (C₁-C₆) alkyl, piperidinyl, or piperazinyl, which piperidinyl or piperazinyl is optionally substituted with pyridyl; or R³ and each R⁴ taken together with the nitrogen to which they are attached form a 3, 4, 5, 6, 7, 8, or 9 membered ring that is optionally substituted with one or more groups independently selected from the group consisting of halo;

R⁵ is a 4-7 membered heterocyclyl;

Y is S, O, or Se;

each $R^a$ is independently selected from the group consisting of H, (C₁-C₆) alkyl, (C₂-C₆) alkenyl, (C₂-C₆) alkynyl, (C₃-C₆) cycloalkyl, (C₁-C₆) alkanoyl, and (C₁-C₆) alkoxycarbonyl, wherein any (C₁-C₆) alkyl, (C₂-C₆) alkenyl, (C₂-C₆) alkynyl, (C₃-C₆) cycloalkyl, (C₁-C₆) alkanoyl, and (C₁-C₆) alkoxycarbonyl, (C₂-C₆) alkoxycarbonyl, (C₂-C₆) alkylaminocarbonyl, and (C₂-C₆) alkanoylamino is optionally substituted with one or more groups independently selected from halo, (C₃-C₆) cycloalkyl, and (C₁-C₆) alkoxy; or two $R^a$ taken together with the nitrogen to which they are attached form a azetidino, pyrrolidino, piperidino, or morpholino ring; and each $R^b$ is independently selected from the group consisting of H, (C₁-C₆) alkyl, (C₃-C₆) alkenyl, (C₃-C₆) alkynyl, (C₃-C₆) cycloalkyl, (C₁-C₆) alkanoyl, (C₁-C₆) alkylaminocarbonyl and (C₁-C₆) alkoxycarbonyl, wherein any (C₁-C₆) alkyl, (C₃-C₆) alkenyl, (C₃-C₆) alkynyl, (C₃-C₆) cycloalkyl, (C₁-C₆) alkanoyl, and (C₁-C₆) alkoxycarbonyl, (C₁-C₆) alkylaminocarbonyl, and (C₂-C₆) alkanoylamino is optionally substituted with one or more groups independently selected from halo, (C₃-C₆) cycloalkyl, and (C₁-C₆) alkoxy; or two $R^a$ taken together with the nitrogen to which they are attached form a ring, e.g., azetidino, pyrrolidino, piperidino, or morpholino;

provided the compound of formula (I) is not:

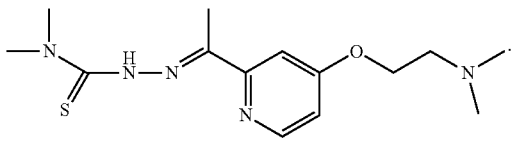

2. The complex of claim 1 comprising $Zn^{2+}$ and a compound of formula (I):

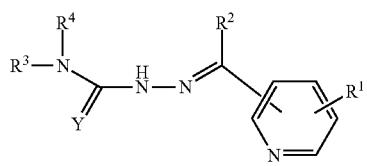

(I)

or a deuterated analog thereof, or an ion or poly-ion thereof, or a salt of said complex, wherein:

R¹ is (C₁-C₆) alkoxy or (C₃-C₆) cycloalkyoxy, wherein any (C₁-C₆) alkoxy or (C₃-C₆) cycloalkyoxy is substituted with one or more groups independently selected —N($R^a$)₂ and (C₁-C₆) alkoxy;

R² is selected from the group consisting of H, phenyl, heteroaryl, (C₁-C₆) alkyl, (C₂-C₆) alkenyl, (C₂-C₆) alkynyl, and (C₃-C₆) cycloalkyl, wherein any phenyl, heteroaryl, (C₁-C₆) alkyl, (C₂-C₆) alkenyl, (C₂-C₆) alkynyl, and (C₃-C₆) cycloalkyl and C₄-C₆-heterocyclealkyl, is optionally substituted with one or more groups independently selected from halo, —N($R^b$)₂, (C₃-C₆) cycloalkyl, (C₁-C₆) alkoxy, (C₂-C₆) alkanoyloxy, (C₂-C₆) alkoxycarbonyl, (C₂-C₆) alkylaminocarbonyl, and (C₂-C₆) alkanoylamino;

R³ and R⁴ are each independently selected from H, (C₁-C₆) alkyl, piperidinyl, or piperazinyl, which piperidinyl or piperazinyl is optionally substituted with pyridyl; or R³ and each R⁴ taken together with the nitrogen to which they are attached form a 3, 4, 5, 6, 7, 8, or 9 membered ring that is optionally substituted with one or more groups independently selected from the group consisting of halo;

Y is S, O, or Se;

each $R^a$ is independently selected from the group consisting of H, (C₁-C₆) alkyl, (C₂-C₆) alkenyl, (C₂-C₆) alkynyl, (C₃-C₆) cycloalkyl, (C₁-C₆) alkanoyl, and (C₁-C₆) alkoxycarbonyl, wherein any (C₁-C₆) alkyl, (C₂-C₆) alkenyl, (C₂-C₆) alkynyl, (C₃-C₆) cycloalkyl, (C₁-C₆) alkanoyl, and (C₁-C₆) alkoxycarbonyl, (C₂-C₆) alkoxycarbonyl, (C₂-C₆) alkylaminocarbonyl, and (C₂-C₆) alkanoylamino is optionally substituted with one or more groups independently selected from halo, (C₃-C₆) cycloalkyl, and (C₁-C₆) alkoxy; or two $R^a$ taken together with the nitrogen to which they are attached form a azetidino, pyrrolidino, piperidino, or morpholino ring; and each $R^b$ is independently selected from the group consisting of H, (C₁-C₆) alkyl, (C₃-C₆) alkenyl, (C₃-C₆) alkynyl, (C₃-C₆) cycloalkyl, (C₁-C₆) alkanoyl, (C₁-C₆) alkylaminocarbonyl and (C₁-C₆) alkoxycarbonyl, wherein any (C₁-C₆) alkyl, (C₃-C₆) alkenyl, (C₃-C₆) alkynyl, (C₃-C₆) cycloalkyl, (C₁-C₆) alkanoyl, and (C₁-C₆) alkoxycarbonyl, (C₁-C₆) alkylaminocarbonyl, and (C₂-C₆) alkanoylamino is optionally substituted with one or more groups independently selected from halo, (C₃-C₆) cycloalkyl, and (C₁-C₆) alkoxy; or two $R^a$ taken together with the nitrogen to which they are attached form a ring, e.g., azetidino, pyrrolidino, piperidino, or morpholino;

provided the compound of formula (I) is not:

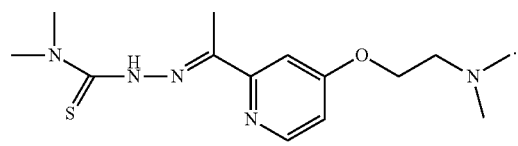

3. The complex of claim 1, wherein R¹ is (C₁-C₆) alkoxy that is substituted with one or more groups independently selected —N($R^a$)₂ and (C₁-C₆) alkoxy; or wherein R¹ is (C₁-C₆) alkoxy that is substituted with —N($R^a$)₂.

4. The complex of claim 1, wherein R¹ is (C₁-C₆) alkoxy that is substituted with (C₁-C₆) alkoxy.

5. The complex of claim 1, wherein R¹ is (C₃-C₆) cycloalkyoxy that is substituted with —N($R^a$)₂ or (C₁-C₆) alkoxy.

6. The complex of claim 1, wherein R¹ is (C₁-C₆) alkoxy or (C₃-C₆) cycloalkyoxy, wherein any (C₁-C₆) alkoxy or (C₃-C₆) cycloalkyoxy is substituted with one or more groups independently selected from —N($R^a$)₂ and (C₁-C₆) alkoxy.

7. The complex of claim 1, which is a complex of formula:

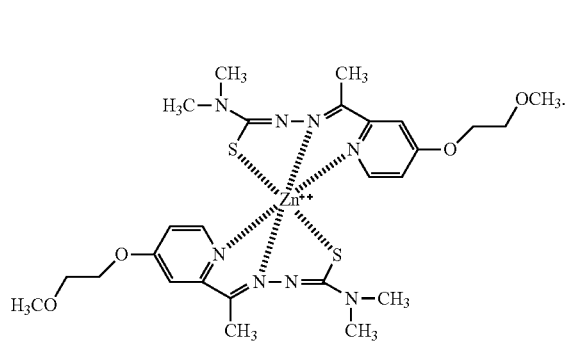

8. The complex of claim 1, which is a complex of formula:

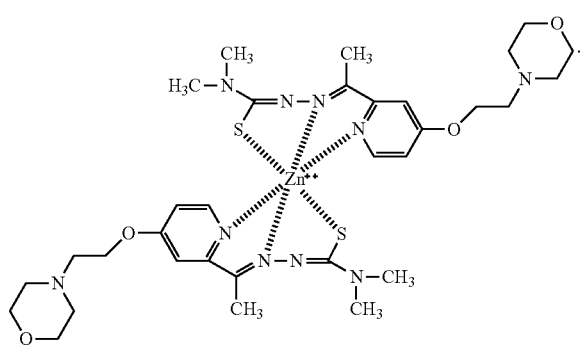

9. The salt of claim 1, which is:

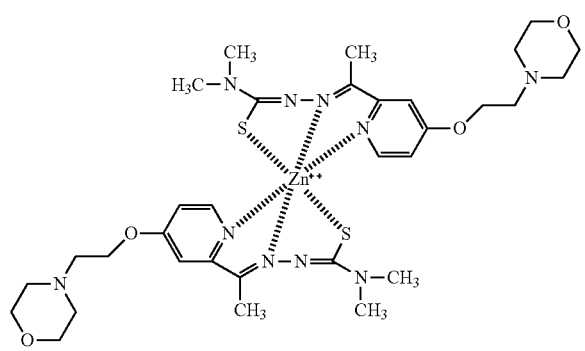

bis mesylate salt.

10. The complex of claim 1, which is a complex of formula:

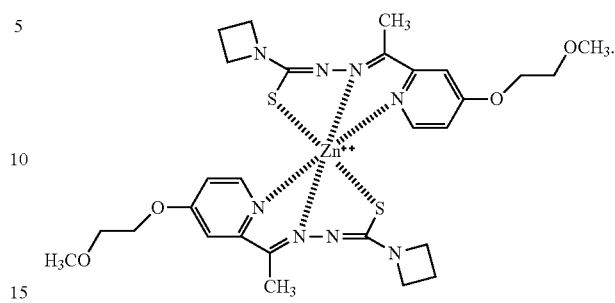

11. The complex of claim 1, which is a complex of formula:

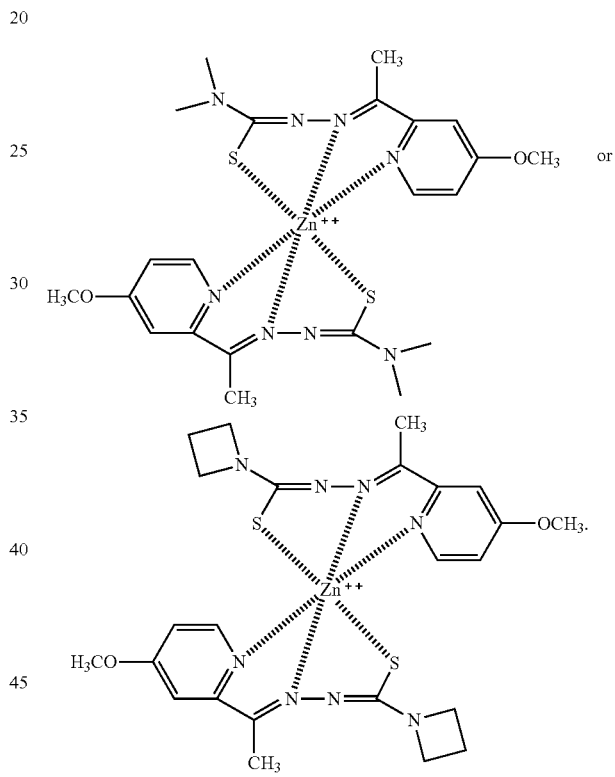

or

12. The complex of claim 1, wherein each $R^a$ is independently selected from the group consisting of H, $(C_1-C_6)$ alkyl, $(C_2-C_6)$ alkenyl, $(C_2-C_6)$ alkynyl, $(C_3-C_6)$ cycloalkyl, $(C_1-C_6)$ alkanoyl, and $(C_1-C_6)$ alkoxycarbonyl, wherein any $(C_2-C_6)$ alkenyl, $(C_2-C_6)$ alkynyl, $(C_3-C_6)$ cycloalkyl, $(C_1-C_6)$ alkanoyl, and $(C_1-C_6)$ alkoxycarbonyl, $(C_2-C_6)$ alkoxycarbonyl, $(C_2-C_6)$ alkylaminocarbonyl, and $(C_2-C_6)$ alkanoylamino is optionally substituted with one or more groups independently selected from halo, $(C_3-C_6)$ cycloalkyl, and $(C_1-C_6)$ alkoxy; and wherein any $(C_1-C_6)$ alkyl is substituted with one or more groups independently selected from halo, $(C_3-C_6)$ cycloalkyl, and $(C_1-C_6)$ alkoxy.

13. The complex of claim 1, wherein two $R^a$ taken together with the nitrogen to which they are attached form a ring, e.g., azetidino, pyrrolidino, piperidino, or morpholino.

14. A pharmaceutical composition, comprising a complex of claim 1 or a solvate thereof, and a pharmaceutically acceptable carrier.
15. The complex of claim 1, which is a complex of formula:
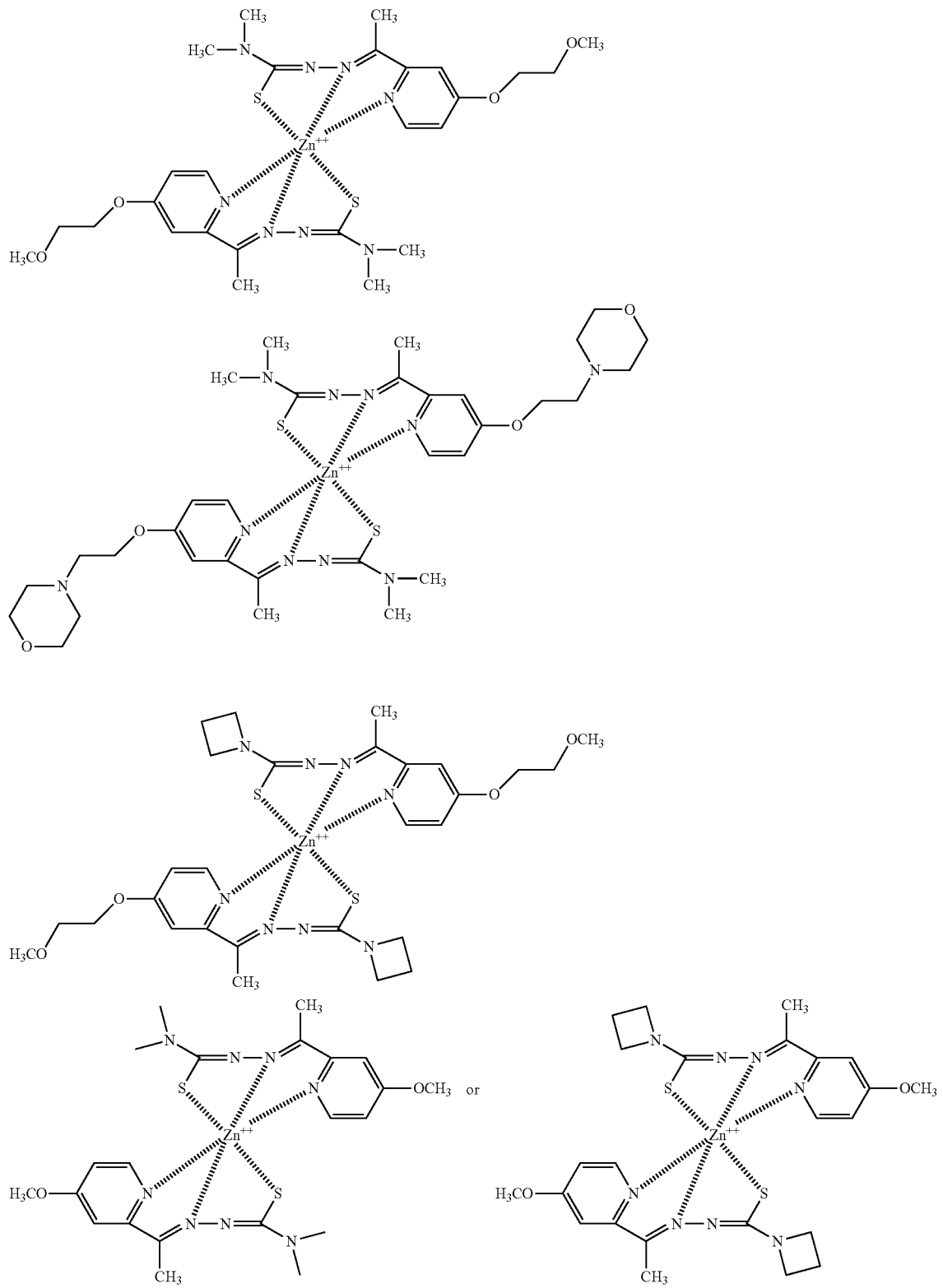

or the salt of claim 1, which is:
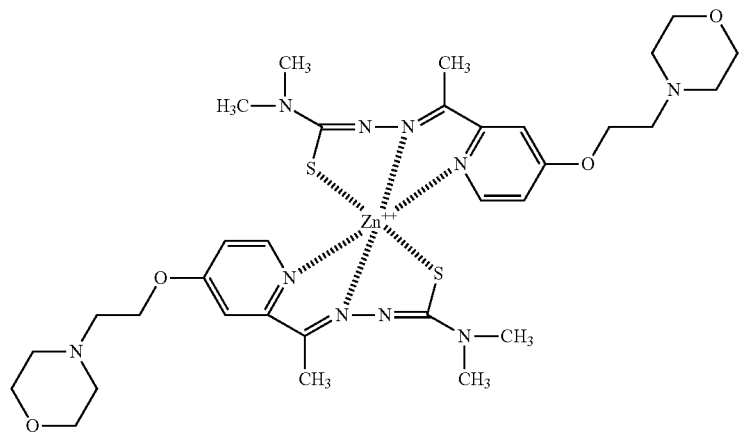
bis mesylate salt.
16. A pharmaceutical composition, comprising a complex or salt of claim 15 or a solvate thereof, and a pharmaceutically acceptable carrier.
* * * * *